(12) United States Patent
Mueller et al.

(10) Patent No.: US 7,491,209 B2
(45) Date of Patent: Feb. 17, 2009

(54) INSTRUMENT GUIDE AND IMPLANT HOLDER

(75) Inventors: Richard Mueller, Macedonia, OH (US); Randall R. Theken, Coventry Township, OH (US); Morton B. Albert, Akron, OH (US)

(73) Assignee: Theken Spine, LLC, Akron, OH (US)

( * ) Notice: Subject to any disclaimer, the term of this patent is extended or adjusted under 35 U.S.C. 154(b) by 0 days.

(21) Appl. No.: 11/358,982

(22) Filed: Feb. 22, 2006

(65) Prior Publication Data

US 2006/0155298 A1 Jul. 13, 2006

Related U.S. Application Data

(62) Division of application No. 10/384,202, filed on Mar. 7, 2003, now Pat. No. 7,278,997.

(51) Int. Cl.
*A61B 17/58* (2006.01)
(52) U.S. Cl. ..................................................... 606/104
(58) Field of Classification Search ............ 606/63–68, 606/72–75, 95, 98, 99, 104
See application file for complete search history.

(56) References Cited

U.S. PATENT DOCUMENTS 7,094,242 B2 * 8/2006 Ralph et al. ................... 606/96

* cited by examiner

*Primary Examiner*—William H. Matthews
(74) *Attorney, Agent, or Firm*—Robert H. Eichenberger; Middleton Reutlinger

(57) ABSTRACT

An instrument guide and implant holding device is provided which releasably secures an implant to the instrument guide. The device provides a convenient guide for surgeons to perform various operative techniques on the subject bone without the need for separate devices, and allows all these operative techniques to be performed without removing the instrument guide from the dissected area until all operative techniques have been completed. The releasable mechanism allows the surgeon to easily hold the instrument to an implant using a simple press-fit approach, and easily releases from the implant with a minimal amount of force. An embodiment also allows the surgeon to releasably lock the cannula in a given orientation about the centroidal axis of the implant fastener hole.

24 Claims, 32 Drawing Sheets

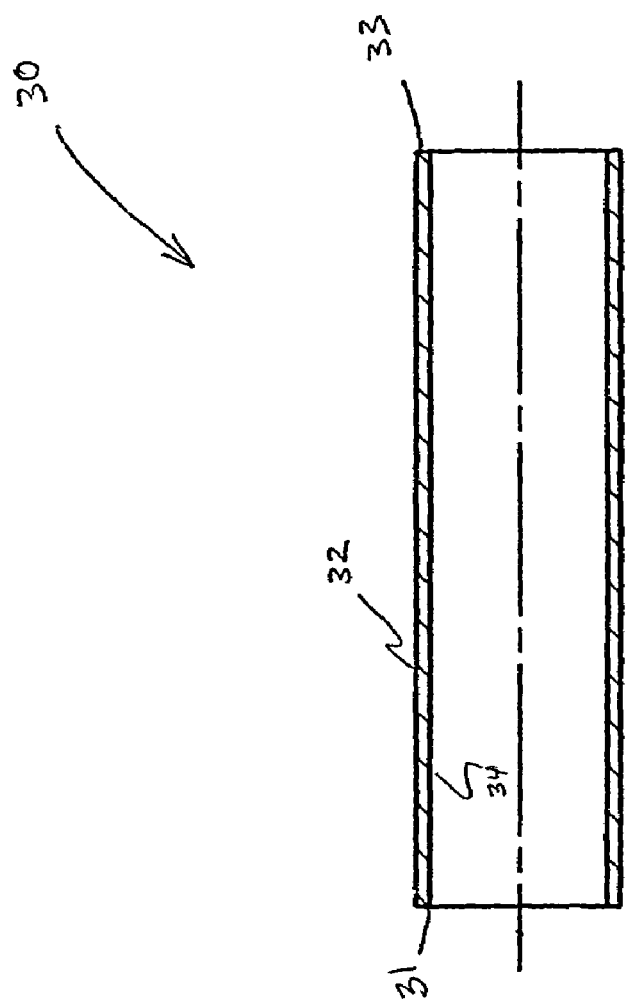
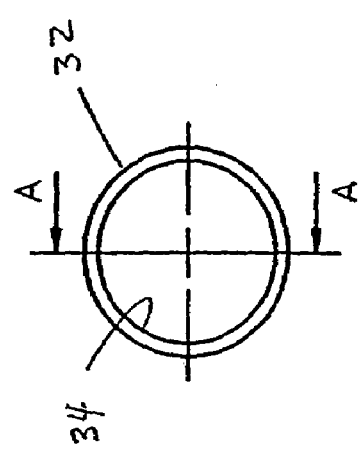
FIG. 4(b)
FIG. 4(a)

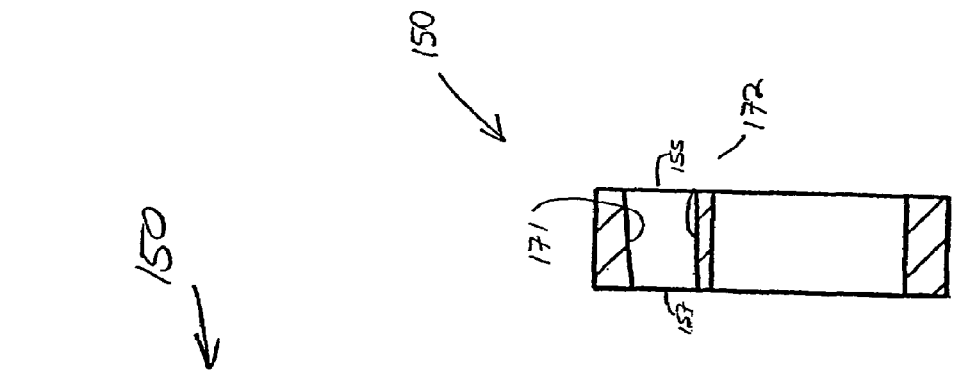
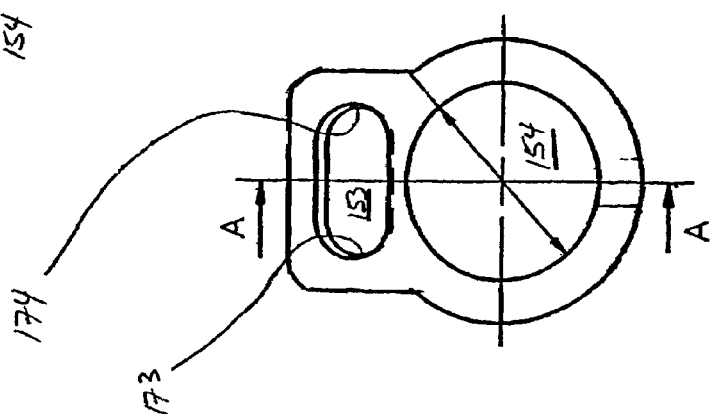
FIG. 15
FIG. 16
FIG. 17

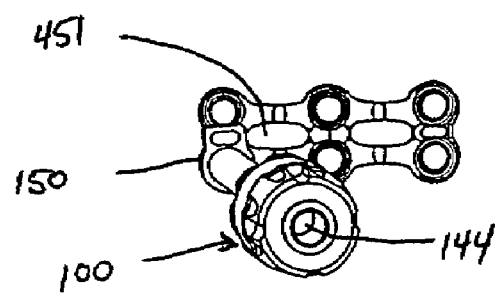
FIG. 23
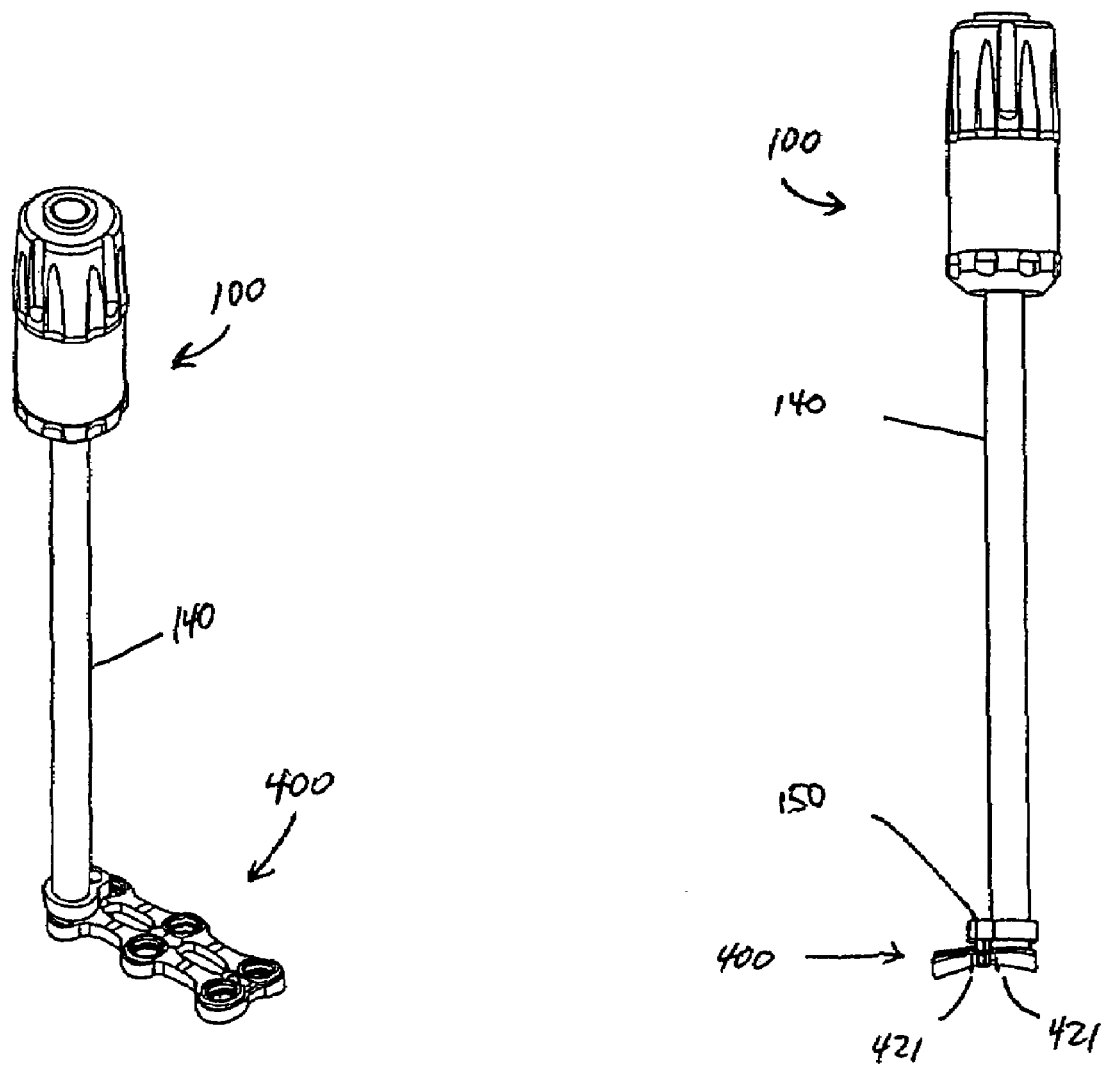
FIG. 22
FIG. 24

SECTION A-A

INSTRUMENT GUIDE AND IMPLANT HOLDER

CROSS-REFERENCE TO RELATED APPLICATION

This application is a divisional application of and claims priority to U.S. application Ser. No. 10/384,202, filed on Mar. 7, 2003, now U.S. Pat. No. 7,278,997.

BACKGROUND OF THE INVENTION

The present invention relates generally to medical instrumentation for implanting medical devices. More particularly, the invention relates to an instrument guide and holder assembly that can be used in conjunction with orthopedic plate systems.

In the art of orthopedic fixation, it has become common for surgeons to utilize fixation plates for the treatment of spinal disorders including spinal anomalies, spinal injuries, disc problems, and bone problems. Indeed, within the past several years, the use of fixation plates for the treatment of spinal disorders or for fusion of vertebrae has grown considerably, and spinal plates have found increased use and desirability in the cervical spine as well.

As adequately described by Dr. Howard S. An and Dr. Jerome M. Cotler in the publication entitled *Spinal Instrumentation*, the upper cervical spine can be approached either anteriorly or posteriorly, depending upon the spinal disorder to be treated. This text discusses the fact that severe complications associated with procedures involving the upper cervical spine can be catastrophic, including injuries to the brain stem, spinal cord, or vertebral arteries, not to mention damage to the esophagus. These complications for upper cervical spine procedures are in addition to the normal complications associated with exposure and fusion of the cervical spine, implantation of a spinal fixation plate, and general disturbance of the spine.

In procedures involving the cervical spine, additional difficulties are encountered as a direct result of the small space in which the surgeon has to operate. When the upper cervical area is dissected, surgeons often find it difficult to maneuver because dissection is intimately close to vital neural, vascular, and visceral structures. As a result, surgeons have little room to operate, and even less room to manually position bone implant structures. Couple this with the fact that the surgeon typically seeks to minimize the time in which the spine is exposed, and the result is a need for bone implant assemblies and their related medical instrumentation to allow for rapid and accurate placement of the bone implant.

In certain procedures requiring variable angle fixation (that is, insertion of fasteners that are allowed to have varying angles of entry to allow settling and movement in situ) surgeons sometimes have difficulty maintaining consistency when performing multiple operative techniques through a given variable through-hole. For instance, when attempting to drill, tap, and insert a variable angle screw in a bone implant through an instrument guide, slight movements in the instrument guide that occur between or during these separate operative techniques can result in misaligned threads, stripped threads, and overall generalized weakened fastening. As a result, the need exists for an instrument guide that can lock the variable cannula in place to facilitate the multiple operative techniques that must be performed therethrough.

Several prior art devices have attempted to provide an instrument and/or a plating system to accurately and quickly locate a bone plate at the proper location on the target bone. Many systems employ the use of multiple component devices: a device that acts as a guide to drill the holes; a device to tap the bone via the hole; and a device that inserts the screw into the plate and bone through the holes created by the first two devices. Using multiple instruments can be time-consuming and aggravating to the surgeon. In addition, inserting and removing separate devices in the small exposed surgical area increases the likelihood of damage to the surrounding tissue.

Additionally, many prior art devices lack an appropriate mechanism to releasably secure the instrument guide to the implant. Problems related to these prior art devices generally fall into two categories: those that provide no mechanism for securing the guide to the implant, and those that provide a mechanism that gives too much of a positive locking force. In addition, these instruments in the prior art typically are provided with handles that are offset at some distance from the longitudinal axis of the screw holes. Unfortunately, these systems are cumbersome, time-consuming, and provide very little visual feedback for the surgeon to assist in the procedure.

Therefore a need exists for a medical instrument guide that can rapidly, adequately, and safely locate a bone implant at the desired area. In addition, the need exists for a medical instrument that facilitates all the surgical or operative procedures that a surgeon may employ in implanting a plate, including puncturing, drilling, tapping, verifying hole depth, and fixating a bone screw through a bone plate into a bone that can be done with one versatile instrument. Ideally, these should be capable of being done using a single instrument that need not be removed from the dissected area until these procedures have been completed.

BRIEF SUMMARY OF THE INVENTION

Accordingly, the present invention is directed to an instrument guide and implant holder that can securely and accurately position a bone plate or implant at a target location, while also providing a guide mechanism for properly drilling or tapping a bone screw hole and threading a bone screw into said hole. Use of the present invention allows the surgeon to securely hold the plate at its proper location for insertion into the surgical opening, while still maintaining visibility in the operating region. The present invention is directed to any form of implant at any location in the body, including, for example, implants in the lumbar region, thoracolumbar region, thoracic region, cervical region, as well as non-spinal regions. Similarly, the device is capable of maintaining a fixed angle to the plate for fixed angle bone screw insertion, and also allows for a variable angle to the plate for variable angle bone screw insertion. Likewise, an embodiment of the present invention allows the surgeon to releasably lock the instrument guide at a predetermined variable angle to better facilitate variable angle bone screw insertion.

The device according to one fixed guide embodiment comprises, generally, a guide handle having a proximal end and a distal end and an annular cylindrical cavity therethrough; a cannula also having a proximal and a distal end; and an engaging device located at the distal end of the cannula. In use, the cannula is inserted into the annular cylindrical cavity in the handle. The engaging device is mounted at the distal end of the cannula. In the preferred embodiment, the engaging device actually comprises two members: a base and a tag. The base is affixed (via welding, adhesives, threads, friction fit, and the like) at or near the distal end of the cannula. The tag is then affixed to the base by standard means (again, welding, adhesives, and the like). The engaging device releasably engages a mating opening in a bone implant.

The variable angle guide/holder device comprises the same main elements as the fixed holder device, but has a modified engaging device base and cannula. In the variable angle embodiment, the distal end of the cannula comprises a narrow collar section fitted on its distal end with an outwardly partially spheroidally curved section (ball). This ball mates with a partially spheroidal undercut in the variable base, creating a form of ball and socket design that allows variability in angles of entry (measured conically about the centroidal axis of the through-hole) ranging from approximately 1° to approximately 40°. Preferably, the allowed angulation is limited to about 12° (that is, 6° cone angle per side).

The narrow collar fits inside the annular cylindrical eye of the base, and the spheroidal surface allows angular rotation about the longitudinal axis of the cannula shaft from the spherical center. This allows the surgeon greater ability to alter the direction of the bone screw entry. In the preferred embodiment, the annular cylindrical eye of the base can be fitted with a stop mechanism to prevent or limit movement in any given direction. Ideally, a stop mechanism is provided to prevent movement past vertical in the anterior-posterior direction in order to prevent divergence of the screws.

An alternative embodiment of the invention includes an optional instrument guide extension designed to offset the instrument guide device from the dissected site. The instrument guide extension comprises: a) a handle having a proximal end and a distal end; b) a bent rod having a proximal end and a distal end wherein the proximal end of the bent rod is attached to the distal end of the handle; and c) a subassembly comprising a cylindrical collar having an opening therethrough. The opening through the collar has an entrance and an exit, and the opening is tapered from a first diameter at its entrance to a second diameter at its exit. Preferably, the first diameter is greater than the second diameter.

The device according to a variable guide embodiment of the invention includes a variable cannula locking instrument guide comprising a variable cannula having (a) a partially spheroidal ball section at its distal end; (b) a draw rod having a proximal end and a distal end wherein the proximal end has an enlarged head and the distal end has a threaded section; (c) a draw rod cannula for receiving the draw rod, wherein the draw rod cannula also has a proximal end and a distal end and wherein the proximal end receives a handle; and (d) an engaging device base having a top section and a bottom section connected at a fixed support that defines a gap therebetween. The engaging device base has a first through-hole through both the top section and the bottom section for receiving a drill cannula bushing, which has an internal surface that receives the partially spheroidal ball of the variable cannula. The engaging device base further comprises a second through-hole in the top section for receiving a draw rod cannula, and second through-hole in the bottom section coaxial with the second through-hole in the top section, that receives the threaded portion of the draw rod.

The device according to the invention therefore comprises a system for fixating bones that can be described as having an instrument guide and a bone implant, wherein the instrument guide comprises a handle; a cannula having a proximal end and a distal end; and a tapered tag located at a first distance from the longitudinal axis of the cannula. The bone implant further comprises a plate having a plurality of bone screw through-holes and an instrument receiving through-hole located at a second distance from the longitudinal axis of said bone screw through-holes, wherein the tapered tag engages the instrument receiving through-hole.

It can be seen that the devices according to the invention provide a method of locating a bone plate during surgery using an instrument guide, wherein the instrument guide comprises a handle, a cannula having a proximal end and a distal end, and an engaging device located at the distal end of the cannula, and wherein the bone plate further comprises a plurality of bone fixation screw through-holes and at least one instrument receiving through-hole. The method of locating the bone plate during surgery using the instrument guide comprises the steps of: a) inserting the engaging device tag into the instrument receiving through-hole in the bone plate thereby creating a friction fit between the bone plate and the instrument guide; b) positioning the bone plate at the desired location in a dissected area by using the instrument guide; c) inserting a drill through the cannula of the instrument guide; d) drilling a hole into the bone and removing the drill; e) inserting into the cannula a screw driving mechanism that has previously captured a bone screw thereon; f) driving the screw into the bone; g) removing the screw driving mechanism from the cannula; and h) releasing the instrument guide from the bone plate by applying a tensile force normal to the face of the bone plate.

BRIEF DESCRIPTION OF THE DRAWINGS

The teachings of the present invention can be readily understood by considering the following detailed description of the preferred embodiment in conjunction with the accompanying drawings, in which:

FIG. 4(a) is a longitudinal end view of an optional tube insert;

FIG. 4(b) is a side section view of an optional tube insert;

FIG. 15 is a perspective view of a fixed engaging device base according to a preferred embodiment of the present invention;

FIG. 16 is a top view of a fixed engaging device base according to a preferred embodiment of the present invention;

FIG. 17 is a longitudinal cross-section of a fixed engaging device base according to a preferred embodiment of the present invention;

FIG. 22 is a perspective view of the fixed guide attached to the bone implant according to a preferred embodiment of the present invention;

FIG. 23 is a top view of the fixed guide of FIG. 22 attached to a bone plate;

FIG. 24 is a caudal end view of the fixed guide of FIG. 22 attached to a bone plate;

DETAILED DESCRIPTION OF THE PREFERRED EMBODIMENT

While the present invention will be described more fully hereinafter with reference to the accompanying drawings, in which particular embodiments and methods are shown, it is to be understood from the outset that persons of ordinary skill in the art may modify the invention herein described while achieving the functions and results of this invention. Accordingly, the descriptions which follow are to be understood as illustrative and exemplary of specific embodiments within the broad scope of the present invention and not as limiting the scope of the invention. For instance, words such as "bone implant", are used in the general sense and can include bone plates, bone cages, and any other implantable device. Similarly, for ease of description, the following description refers to bone screws. It should be understood, however, that any fastener that is suitable for implantable devices may be substituted for the screw that is described herein, to the extent that such substitution is possible in the appropriate art to which the invention pertains. Additionally, for ease of description and consistency, attention is given to cervical plates; however, it should be noted than any form of bone implant and location is equally applicable. In the following descriptions, like numbers refer to similar features or like elements throughout.

Figure 1:
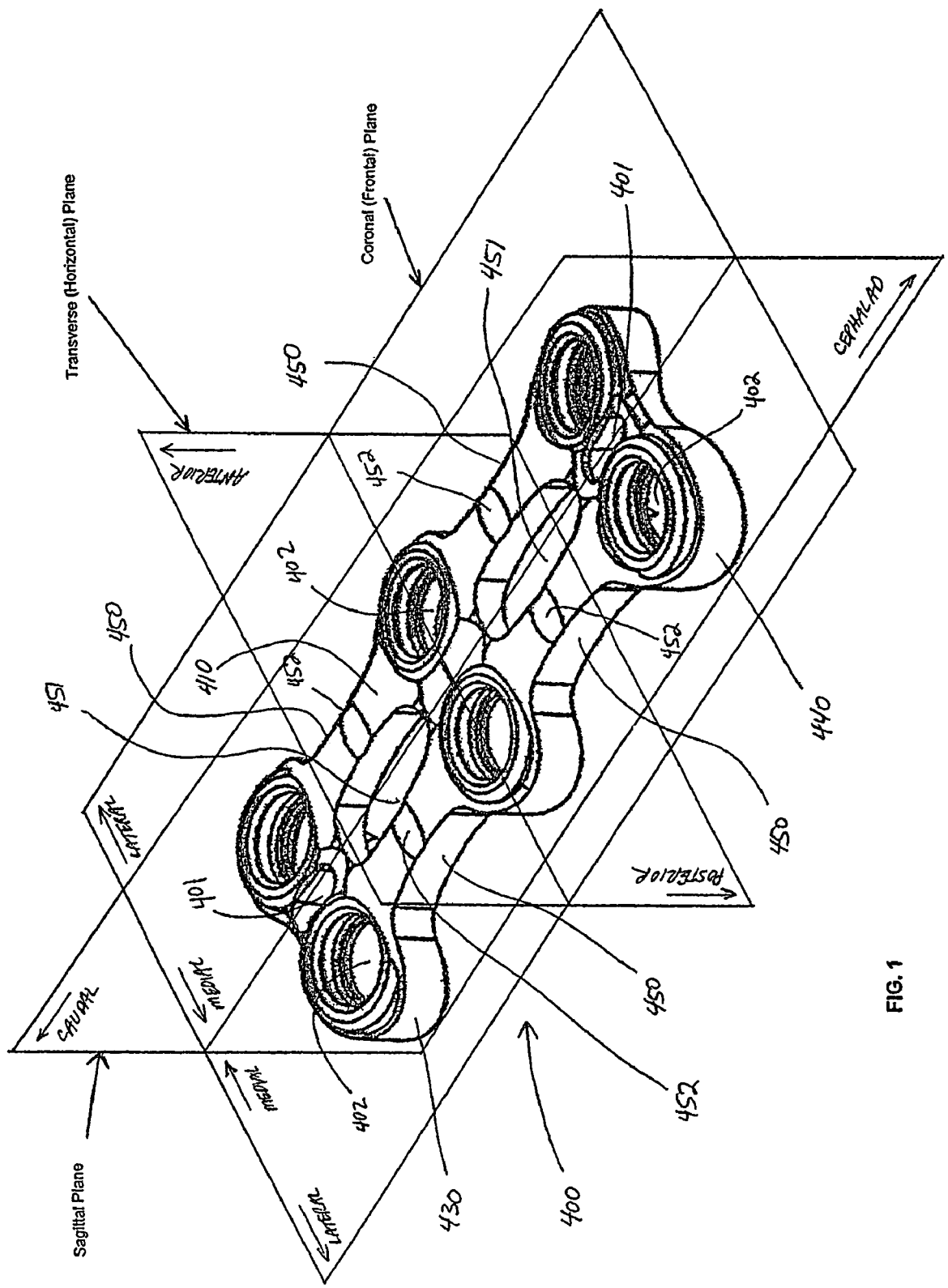
FIG. 1 is a perspective view of a bone implant according to an embodiment of the invention showing reference planes and directional indicators.

The following description may make reference to certain anatomical terminology, reference planes, and directional indicators. FIG. 1 has been provided to facilitate an understanding of the terminology involved. In FIG. 1 a bone implant 400 according to an embodiment of the invention is depicted in perspective view. The bone implant 400 comprises an anterior surface 410 and a posterior surface 420. It can be seen that three mutually orthogonal planes are depicted.

A sagittal plane, generally, divides the bone implant 400 into left and right sides, and a mid-sagittal plane or median plane divides the bone implant into left and right halves. As used herein, unless otherwise noted, any discussion related to a sagittal plane will refer to the mid-sagittal or median plane. Within the sagittal plane an anterior position or direction is defined as upward or in the direction of the anterior surface 410 as drawn in FIG. 1, while a posterior position or direction is defined as downward or in the direction of the posterior surface 420 as drawn in FIG. 1. For this reason the sagittal plane is sometimes referred to as the anterior-posterior plane.

A horizontal or transverse plane divides the bone implant 400 into a top, or cephalad portion and a bottom, or caudal portion. For this reason the horizontal plane may sometimes be referred to as the cephalad-caudal plane.

Finally, a coronal or frontal plane divides the bone implant into a front and a back. Within the coronal plane a medial direction or position is defined as toward the middle of the bone implant 400, while a lateral position or direction is defined as away from the middle of the bone implant 400. For this reason, the coronal plane is sometimes referred to as the medial-lateral plane.

Figure 2:
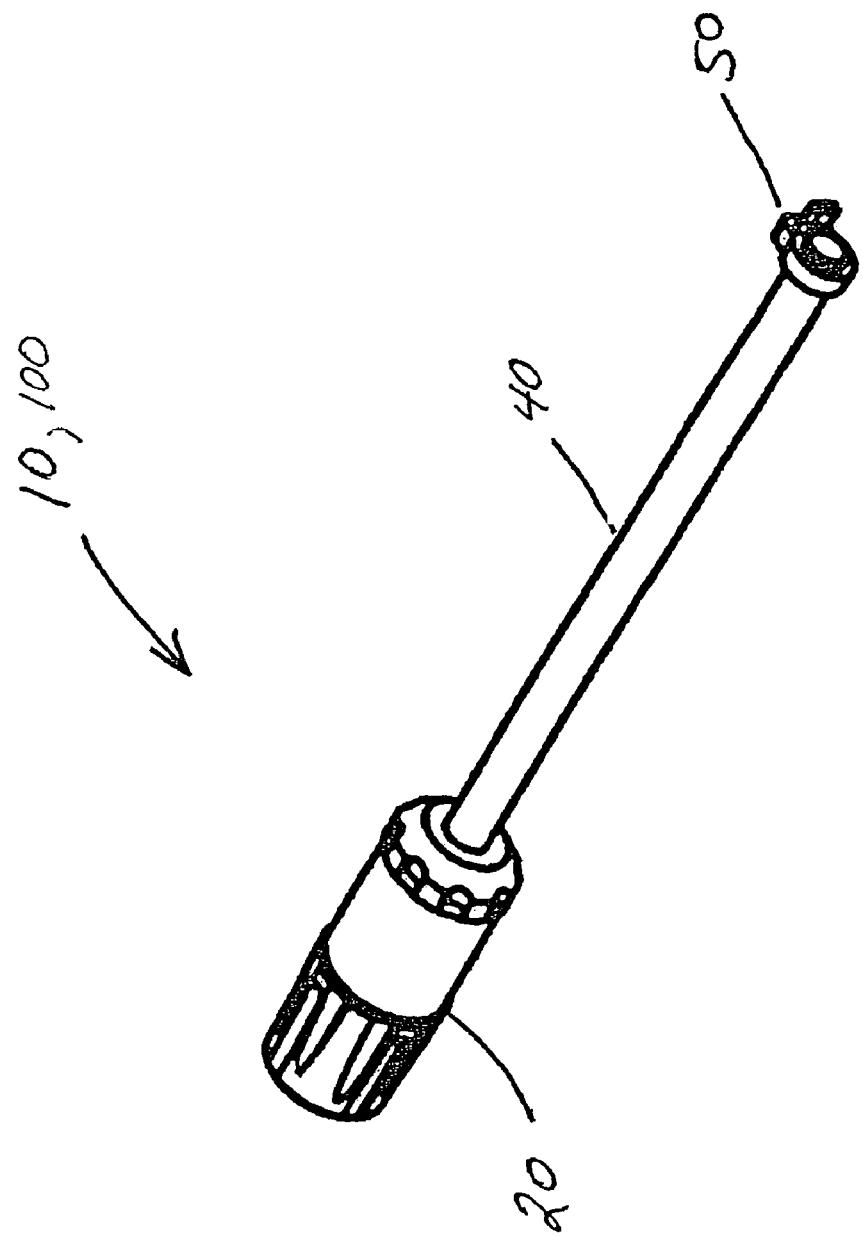
FIG. 2 is a perspective view of a fixed guide embodiment of the present invention.

FIG. 2 depicts, in general form, an instrument guide 10 according to a preferred embodiment. The instrument guide 10 comprises generally a guide handle 20, a cannula 40 and an engaging device 50. In actuality, the instrument guide 10 can be either a fixed guide 100 (components of which are shown in FIGS. 2-7 and 15-21), a variable guide 200 (components of which are shown in FIGS. 25 through 32), or a variable locking guide 500 (components of which are shown in FIGS. 43 through 50). The fixed guide 100 (FIG. 2) is used by surgeons to install fixed angle screws. Similarly, the variable guide 200 (FIG. 25) and variable locking guide 500 (FIG. 43) are used to install variable angle screws which can be installed at various angles of inclination with respect to an imaginary centroidal longitudinal axis of a fastener through-hole 402 in the bone implant 400. Variable screws are desirable in many implant applications because of the differential settlement or movement that is likely to occur after implantation. In certain regions, such differential movement must be accounted for in some fashion to alleviate the resultant increased stresses on the fastening members imposed by such movement.

Fixed Guide 100

Figure 3:
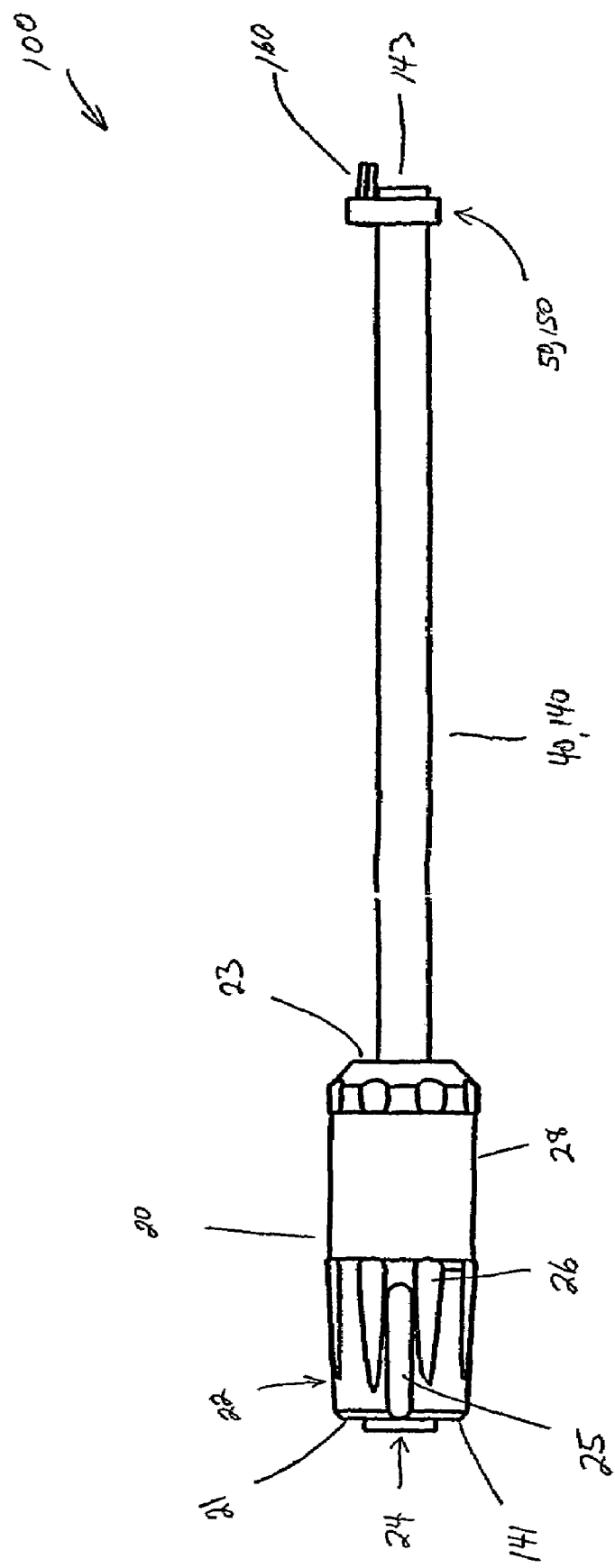
FIG. 3 is an elevation view of the fixed guide embodiment of FIG. 2.

FIG. 3 depicts a fixed guide 100 having a guide handle 20 of a generalized hollow cylindrical shape akin to many handles for hand-held tools. The guide handle 20 typically comprises an outer surface 22 surrounding an inner through-hole or internal cylindrical cavity 24. The outer surface 22 can be of many shapes including ergonomic and non-ergonomic designs. In addition, outer surface 22 can contain many geometrical indentations or appurtenances that improve grip. In the preferred embodiment, outer surface 22 comprises a plurality of longitudinal grooves 26 disposed thereon. In addition, guide handle 20 can include an optional undercut 28 for label attachment, warnings, instructions, or other graphical displays. The guide handle 20 typically has a proximal end 21 and a distal end 23. The guide handle 20 may be made of any materials suitable for use in surgical instrumentation, including but not limited to, high temperature plastics such as that material currently sold under the trade name "Radel"; anodized aluminum; titanium; alloys; or any materials suitable for use in the medical field, preferably including those that can withstand numerous autoclave cycles. The preferred material for guide handle 20 is Radel. In addition, the guide handle 20 can have a plurality of slots 25 machined therein to mate with an optional guide extension 300 (to be discussed below). In the preferred embodiment, the guide handle 20 has four slots 25 spaced 90° apart about the circumference of the guide handle 20.

FIG. 4 depicts an optional tube insert 30 that is generally an annular cylindrical member having an outer surface 32, an internal cylindrical surface 34, a proximal end 31, and a distal end 33. The tube insert 30, if used, is placed inside a cylindrical cavity 24 in the guide handle 20. The tube insert 30 provides a through-hole through which a cannula 40 (to be described below) is inserted. Although the cannula 40 can be inserted directly into the cylindrical cavity 24 in the guide handle 20, it is preferable to provide a tube insert 30. The tube insert 30 protects the surface of the cylindrical cavity 24 of the guide handle 20 from sharp objects such as drills, punches, screws, and so forth that are inserted therethrough, and facilitates a shaft 90 of a screw-driving mechanism 91.

Figure 5:
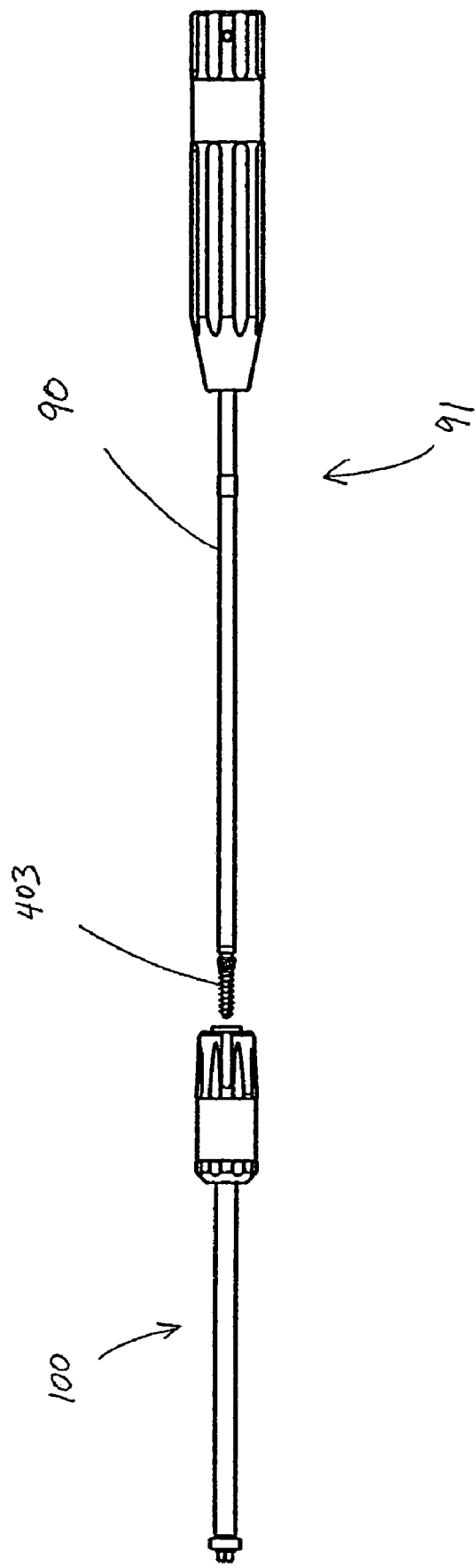
FIG. 5 is an elevation view of a screw driving mechanism with a bone fastener attached being inserted into the fixed guide embodiment.

FIG. 5 depicts a screw driving mechanism 91 with a fastener 403 attached thereto, being inserted into the tube insert 30 within the cylindrical cavity 24 of the guide handle 20. Screw driving mechanism 91 can be of either the fixed or variable type. A fixed screw driving mechanism is used for inserting a fixed screw, while a variable screw driving mechanism is used for inserting a variable screw. In the preferred embodiment of the system, the shaft 90 of the fixed screw driving mechanism 91 will have an outside diameter slightly smaller than both the inside diameter of the tube insert 30 and the fixed cannula 140, but slightly larger than the outside diameter of the variable screw driving mechanism 91 and the variable cannula 240. This prevents the fixed screw driving mechanism from being inserted into the variable guide 200. The interface between the bone implant 400 and implant fastener 403 advantageously prevents the fixed screw from seating in the plate at an angle greater than approximately 0° to 1°. This provides a certain level of safety because fixed screws should not be used in situations requiring a variable angle screw since the stresses created will result in the failure of the implant. On the contrary, however, variable screws may be used in locations requiring a fixed screw. In other words, the outside diameter of the tube insert 30 is dimensioned according to the desired diameter of the cannula 140, 240 (fixed or variable).

Figure 6:
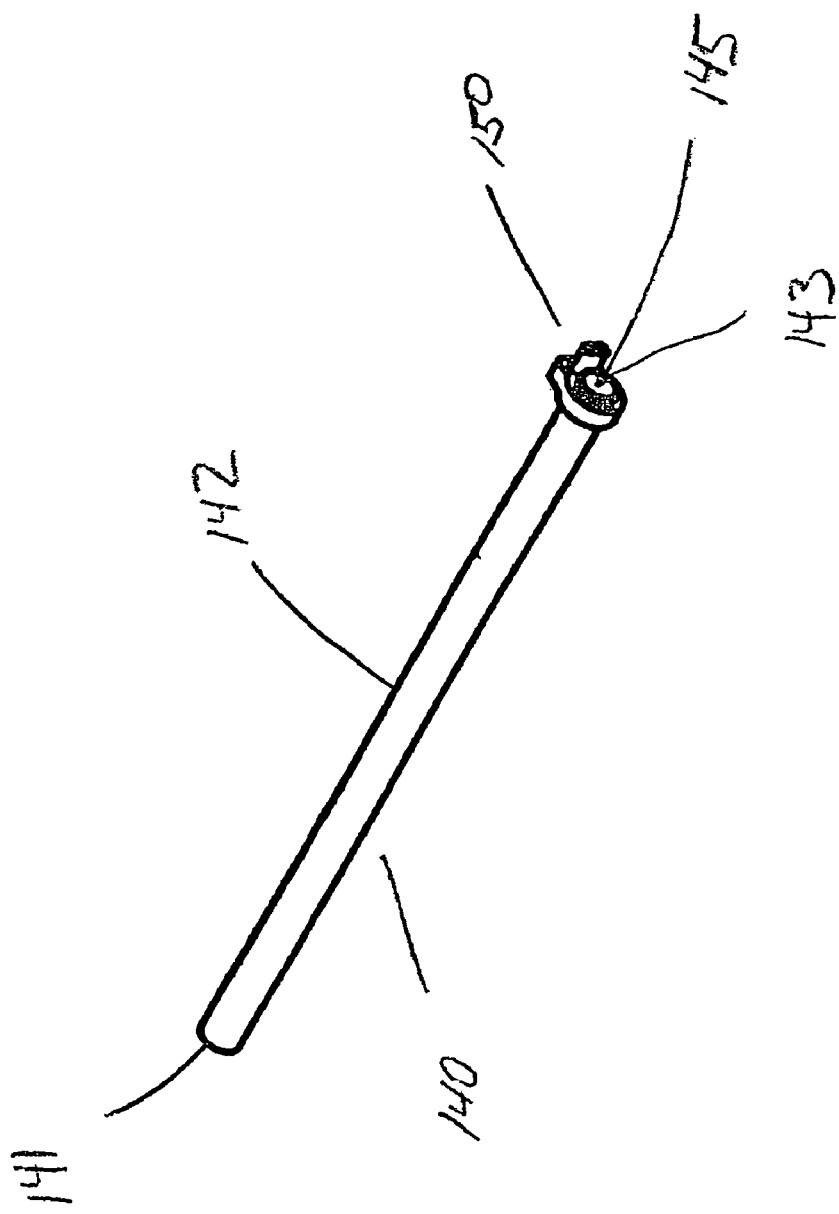
FIG. 6 is a perspective view of a fixed cannula and engaging device according to a preferred embodiment of the present invention.
Figure 7:
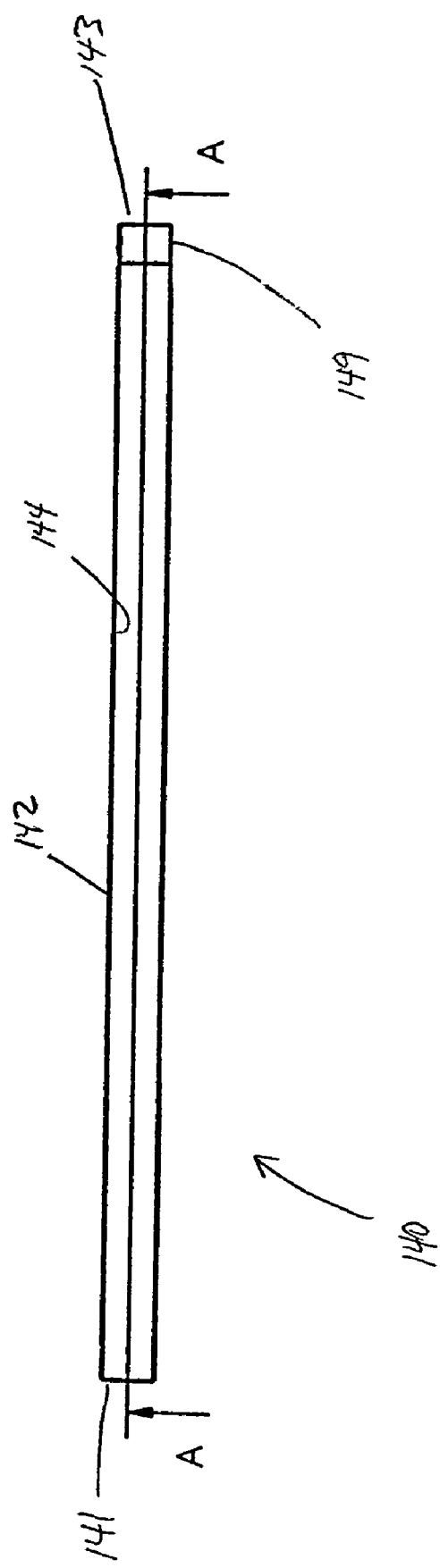
FIG. 7 is an elevation view of the fixed cannula of FIG. 6.
Figure 25:
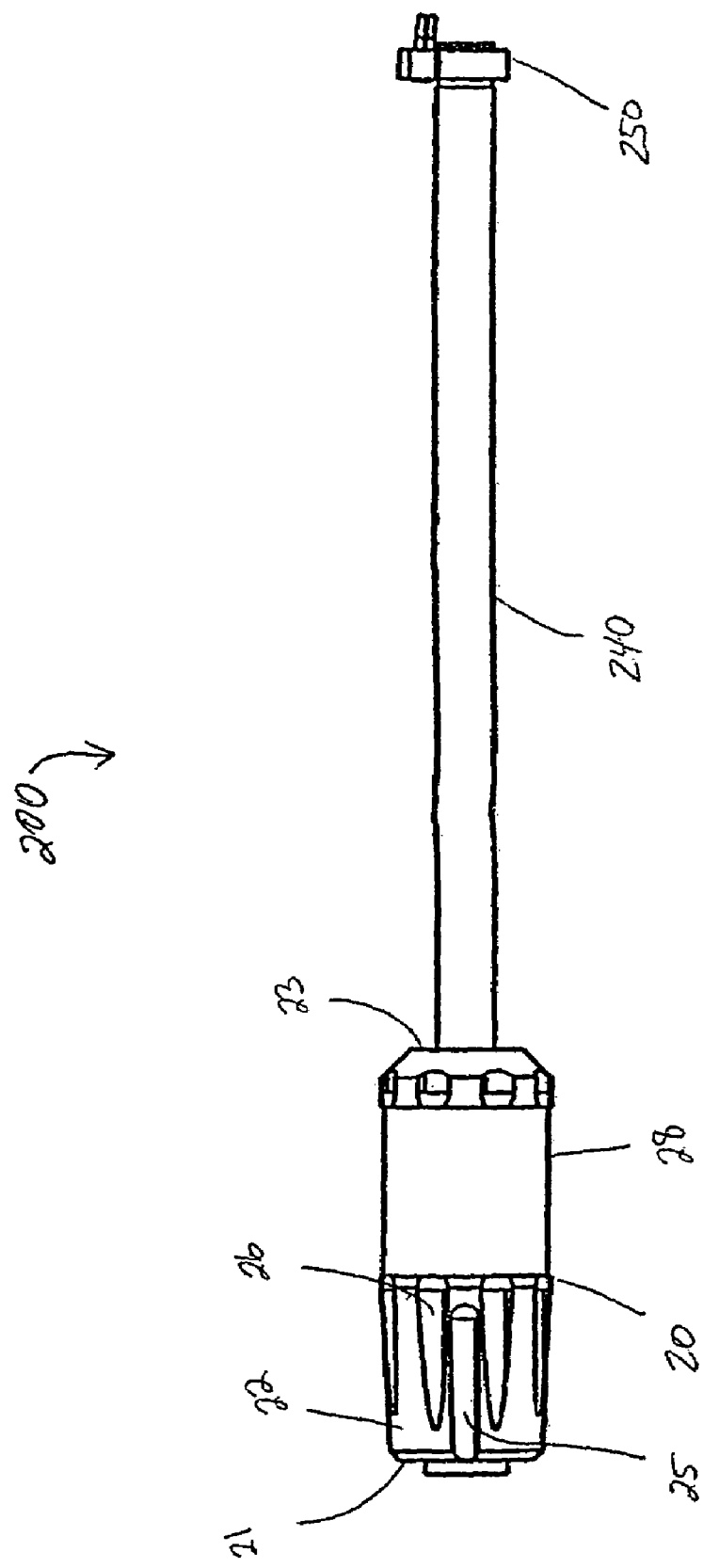
FIG. 25 is an elevation view of a variable guide embodiment of the present invention.
Figure 26:
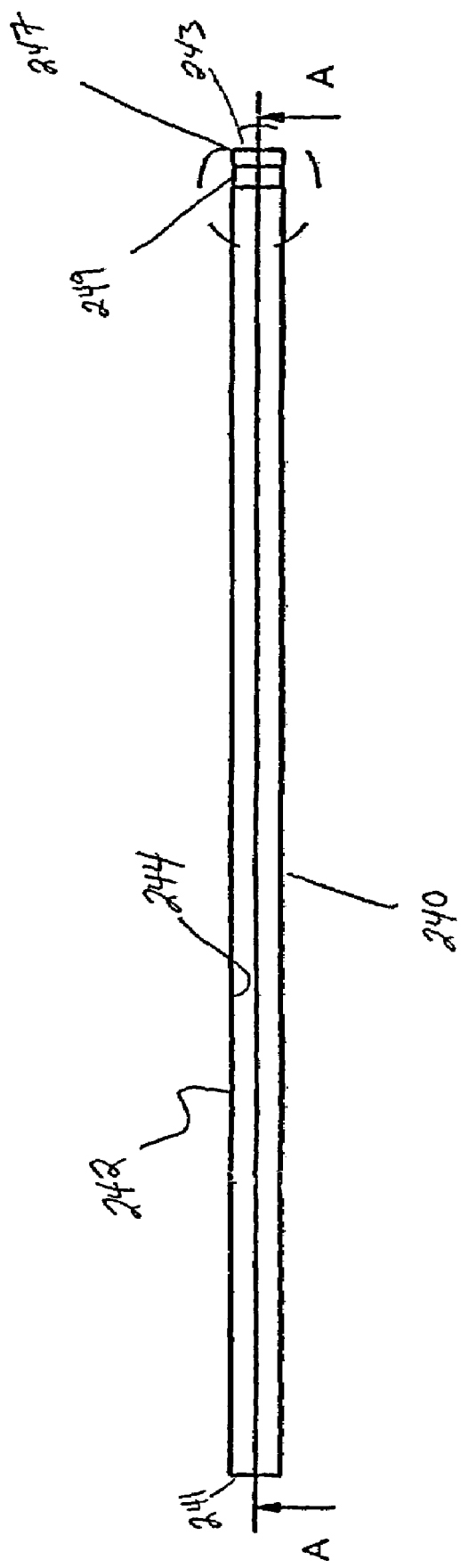
FIG. 26 is an elevation view of a variable cannula according to a preferred embodiment of the present invention.
Figure 31:
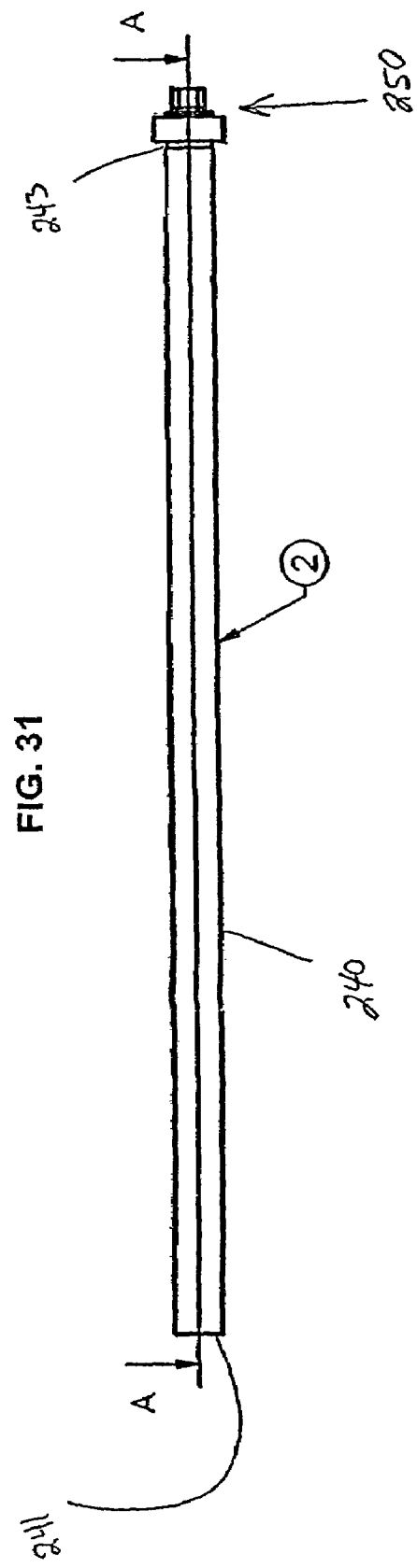
FIG. 31 is a longitudinal elevation view of a variable cannula and variable engaging device according to a preferred embodiment of the present invention.

The cannula 40 is inserted into the guide handle 20 or, if provided, the optional tube insert 30. As mentioned above, the cannula 40 comprises two general designs: a fixed cannula 140 and a variable cannula 240. The fixed cannula 140 is generally depicted in FIGS. 3, 6, and 7. The variable cannula 240 is generally depicted in FIGS. 25, 26, and 31.

Referring first to the figures depicting the fixed cannula 140, it is seen that the fixed cannula 140 comprises a proximal end 141 and a distal end 143, and an outer cannula surface 142 and an inner cannula surface 144. The cannula has an outer diameter that corresponds to the diameter of the outer cannula surface 142 and an inner diameter that corresponds to the diameter of the inner cannula surface 144. The cannula 140 defines the final through-hole 145 through which various medical instruments (such as drills, taps, wires, punches, screws, and screwdrivers) are placed. As a result, the inner diameter of the cannula 140 is greater than the diameter of the medical instruments that pass therethrough. Furthermore, the outer diameter of the cannula 140 is preferably less than the greatest diameter of a fastener through-hole 402 in the bone implant 400 so as to allow the cannula to sit within the fastener through-hole 402.

As shown in FIG. 7, the distal end 143 of the fixed cannula 140 preferably has a section of slightly reduced outside diameter, or collar 149. This is to facilitate attachment to a fixed engaging device base 150 (to be described below). The cannula 140 is typically made from stainless steel, titanium, aluminum, alloys, and any other material having properties that allow for use in surgical techniques and implants.

Figure 8:
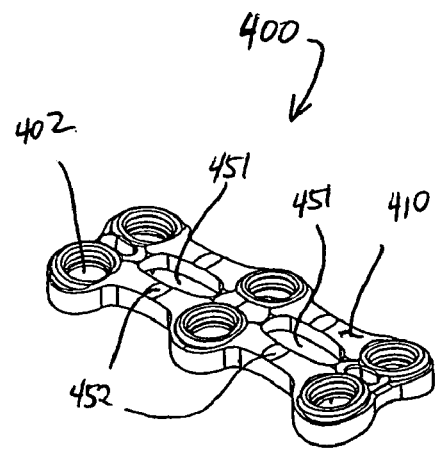
FIG. 8 is a perspective view of a bone implant according to an embodiment of the invention.

FIGS. 8 through 12 depict an embodiment of the bone implant 400 to which the guide 10 of the present invention is readily applicable. That portion of the bone implant 400 and associated structures described at paragraphs 60 through 67 are incorporated by reference herein. FIG. 8 shows a perspective view of a single level bone implant 400 (that is, a bone implant 400 designed to span only one intervertebral disc) having an anterior surface 410 and a posterior surface 420 and a caudal end 430 and a cephalad end 440. The caudal end 430 and the cephalad end 440 are joined by one or more struts 450. One or more fastener through-holes 402 are located at the caudal end 430 and the cephalad end 440. A graft viewing opening 451 is disposed between the caudal end 430 and cephalad end 440.

Figure 9:
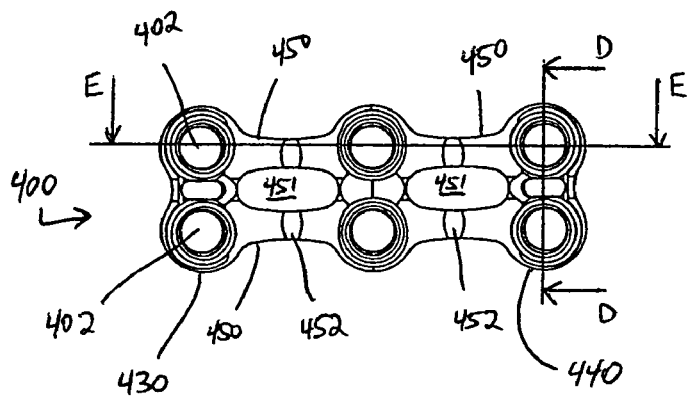
FIG. 9 is an anterior plan view of the bone implant of FIG. 8.

FIG. 9 shows the anterior surface 410 of the bone implant 400 in plan view. An engaging hole 401 is disposed between each fastener through-hole 402 at both the caudal end 430 and the cephalad end 440. One or more pre-machined bend zones 452 is disposed along the length of the struts 450. The bend zones 452 facilitate precision contouring by the physician during surgery. One bend zone 452 is shown in FIG. 9 for the one level bone implant 400, but multiple bend zones would exist in longer 2-level, 3-level, or 4-level bone implants 400.

Figure 10:
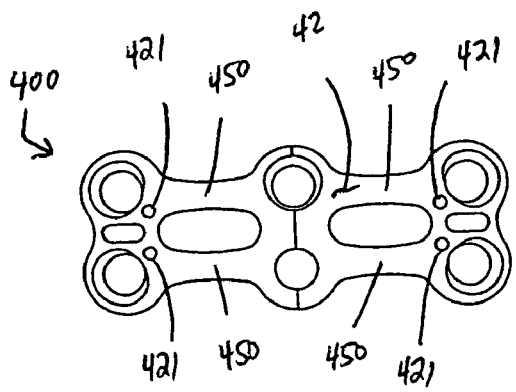
FIG. 10 is a posterior plan view of the bone implant of FIG. 8.
Figure 11:
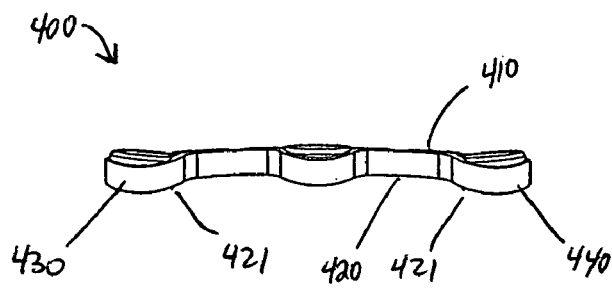
FIG. 11 is a lateral section view of the bone implant of FIG. 8 taken at Section E-E of FIG. 9.

FIG. 10 shows the posterior surface 420 of the bone implant 400. One or more spikes 421 are preferably located on the posterior surface 420 to engage the bone and reduce slippage of the bone implant 400. FIG. 11 is a section view taken along line E-E of FIG. 9. It can be seen that the preferred fastener through-holes 402 have a longitudinal centroidal axis disposed at an angle to the anterior surface 410. This angle of inclination can range from approximately 0° to approximately 40° in a caudal or cephalad direction, depending on the type and location of bone implant 400 used. Ideally, the angles of inclination are such that the fasteners 403 diverge in the caudal-cephalad direction when inserted into the bone implant 400. In the preferred embodiment, this angle of inclination is approximately 10° cephalad and 10° caudal divergent.

Figure 12:
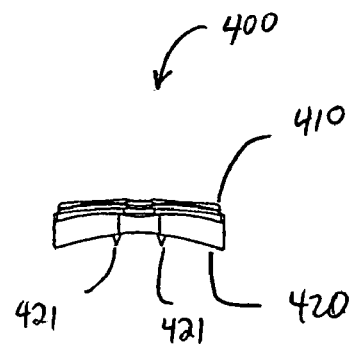
FIG. 12 is a transverse section view of the bone implant of FIG. 8 taken at Section D-D of FIG. 9.
Figure 13:
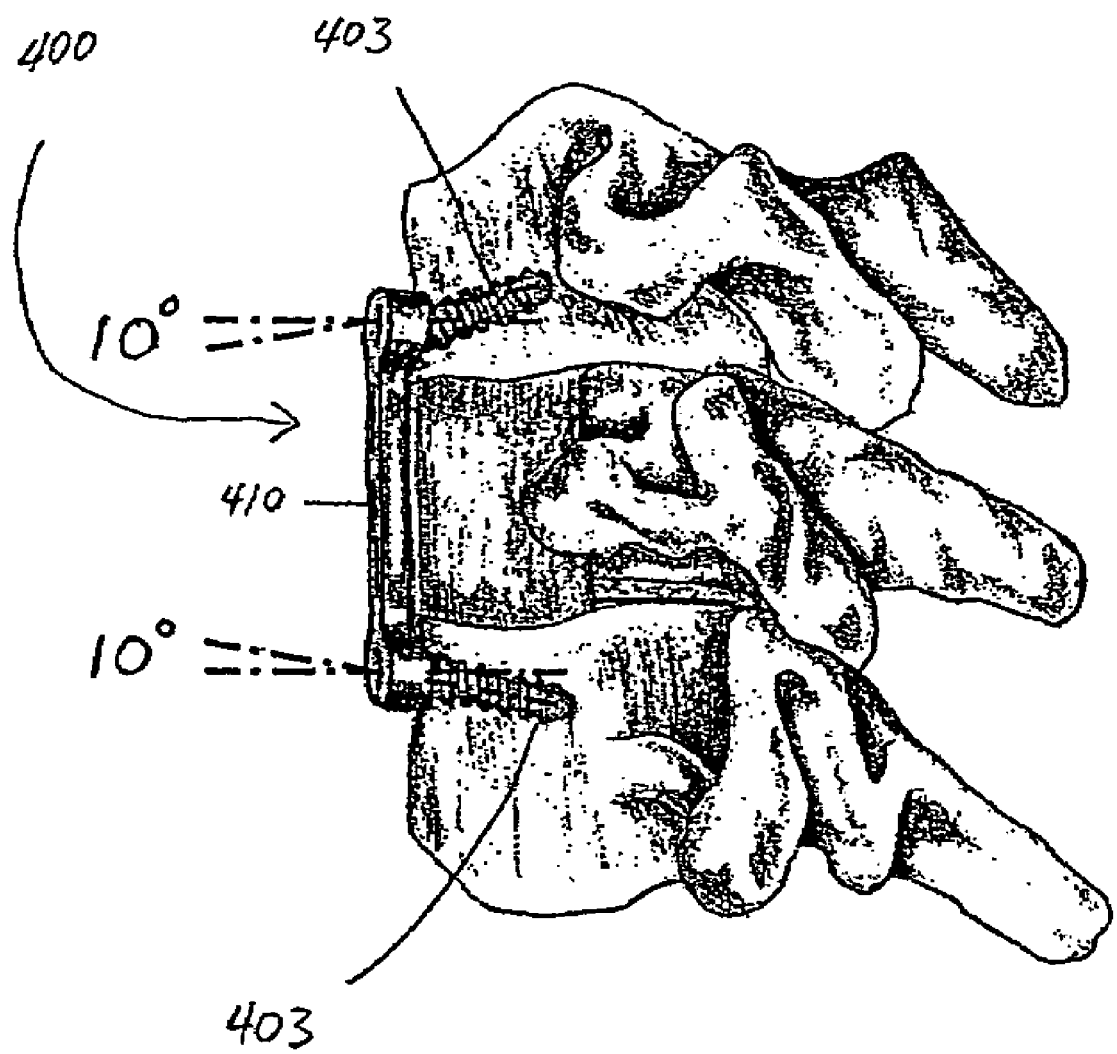
FIG. 13 is a medial-lateral view of a bone implant according to the invention affixed to two cervical vertebrae.
Figure 14:
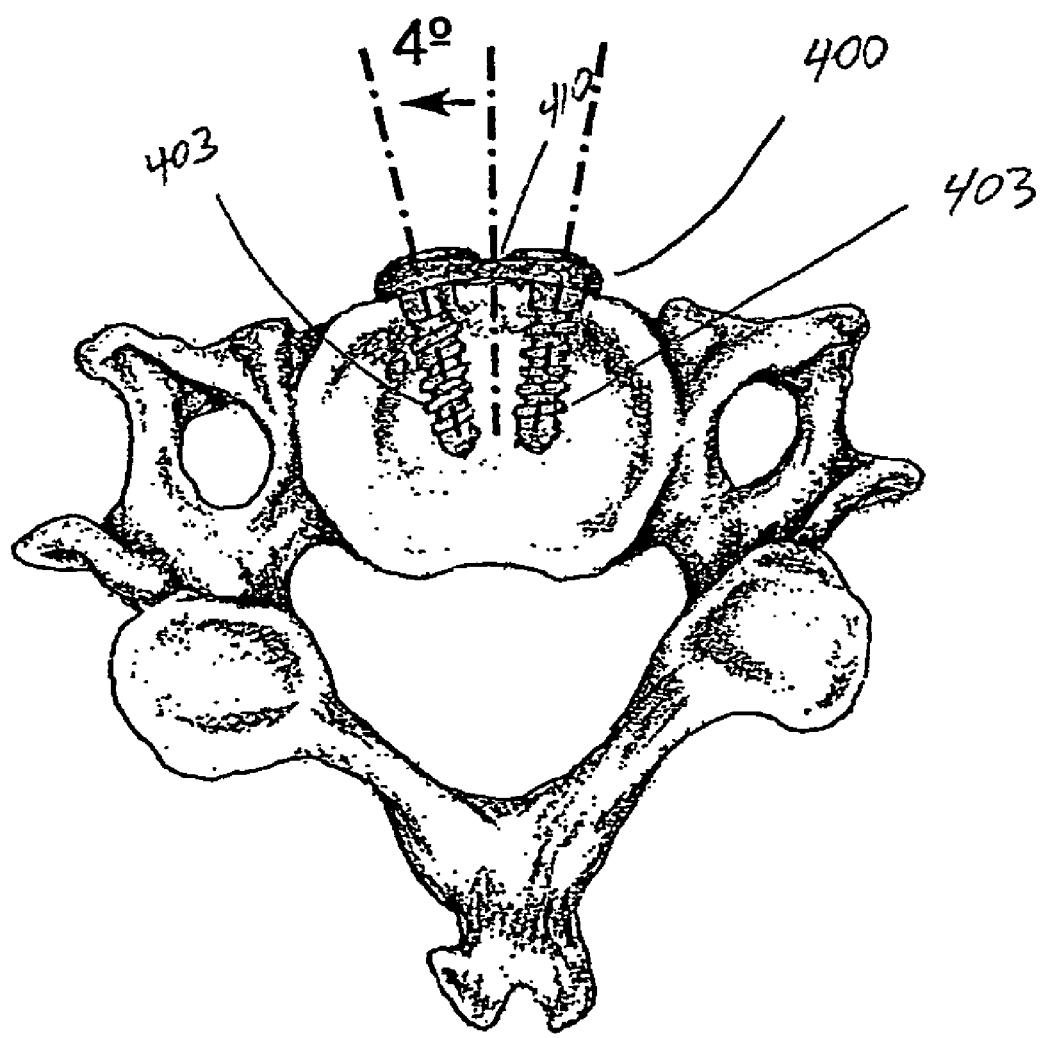
FIG. 14 is a cephalad view of the bone implant of FIG. 13 affixed to the cervical vertebrae.

FIG. 12 is a medial-lateral section view taken along line D-D of FIG. 9. It can be seen that the preferred bone implant 400 has a medial-lateral contour and that the fastener through-holes 402 are provided at a medial-lateral angle of inclination. The medial-lateral contour is included for better anatomical fit to the cervical vertebrae, and the medial-lateral angle of inclination can range from approximately 0° to approximately 5°. In the preferred embodiment the medial-lateral angle of inclination of the centroidal axis of the fastener through-hole 402 is 4°. FIG. 13 shows a medial lateral view of a bone implant 400 affixed to two cervical vertebrae, showing the possibility of a 0° cephalad-caudal angle and a 10° cephalad-caudal divergent angle. FIG. 14 shows a cephalad view of a bone implant 400 installed on a cervical vertebra, showing the preferred 4° medial lateral convergent angle of the fasteners 402.

Now that the bone implant 400 has been described, it is possible to better appreciate the structure and function of the components of the instrument guide 10 that engage the bone implant 400. As mentioned above, the fixed engaging device base 150 comprises two general designs: fixed and variable. FIGS. 15, 16, and 17 best depict the preferred embodiment of the fixed engaging device base 150. The fixed engaging device base 150 has an annular cylindrical eye 154 therethrough at a first end thereof, and a through-hole 153 therethrough at a second end thereof. The through-hole 153 has an entrance 155 and an exit 157 and a centroidal axis therethrough. The through-hole 153 can take any number of configurations so as to preferably be shaped to match the outer profile of an engaging device tag 160 (described below). Such shapes include, but are not limited to: circular, rectangular, ovoidal, or other geometric shape, in addition to a plurality of such holes. In the preferred embodiment, the through-hole 153 takes a generally ovoidal shape. Such may be formed by drilling two separate circular holes at a given distance from the longitudinal axis of the annular cylindrical eye 154, and then milling the material remaining therebetween so as to connect the circumferences of both circular holes with two tangent lines. In fact, the preferred through-hole 153 comprises, in plan view, a rectangular center portion with a semi-circular section in either end. This creates a hole having first and second rectangular sidewalls 171, 172, and first and second semicylindrical sidewalls 173, 174. The annular cylindrical eye 154 is constructed to receive the cannula 140.

Typically, the fixed engaging device base 150 is affixed to the distal end 143 of the cannula 140. In the preferred embodiment, at least one rectangular sidewall 171 or 172 is tapered such that the entrance 155 has a greater dimension than the exit 157. In addition, at least one of the first and second semi-cylindrical sidewalls 173, 174 may be tapered such that the entrance 155 has a greater dimension than the exit 157. No matter whether one or multiple sidewalls, 171, 172, 173, 174 are tapered, together they shall be referred to hereinafter as tapered sidewalls 175. The tapered sidewalls 175 mate with or receive an engaging device tag 160 (described below).

Figure 20:
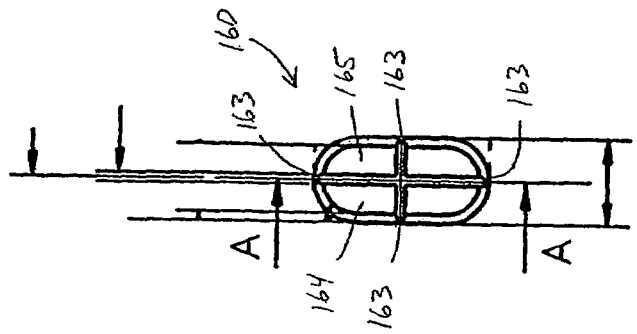
FIG. 20 is a distal end view of the engaging device tag of FIG. 18.
Figure 18:
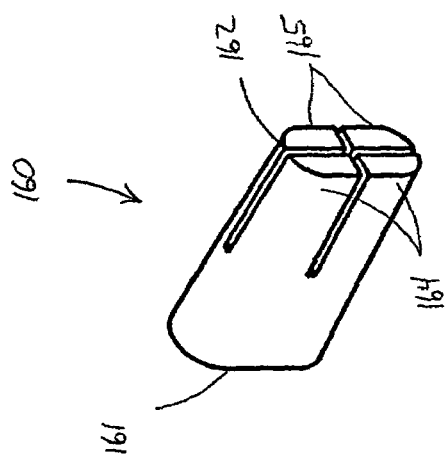
FIG. 18 is a perspective view of an engaging device tag according to a preferred embodiment of the present invention.
Figure 19:
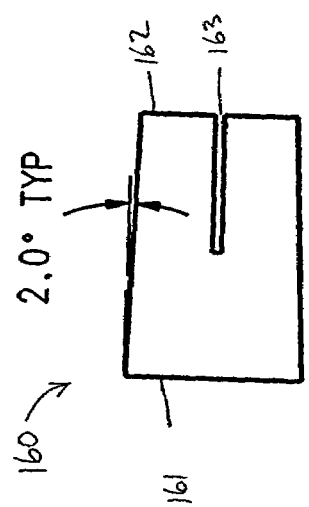
FIG. 19 is an elevation view of the engaging device tag of FIG. 18.

FIGS. 18, 19, and 20 depict the engaging device tag 160, having a proximal end 161 and a distal end 162. The engaging device tag 160 can take many shapes and sizes, having the purpose of releasably engaging the mating engaging hole 401 in the bone implant 400. Any combination of male and female fittings will suffice so long as they create a friction fit that is releasable with little force. In the preferred embodiment, the minimum force necessary to release the engaging device tag 160 is approximately 0.5 lbs, while the maximum force is approximately 3 to 5 lbs. In the preferred embodiment, the engaging device tag 160 is a male tapered tag. The engaging device tag 160 is constructed to match the general shape of the through-hole 153. In the preferred embodiment, the engaging device tag 160, generally comprises a member having a substantially trapezoidal longitudinal section creating a locking taper (see FIG. 19), and a generally ovoidal transverse section (see FIG. 20). This locking taper may have taper angles, in general, of approximately 1° to 5°. Ideally, the angle α depicted in FIG. 19 is approximately 2°. This 2° taper mates with the tapered sidewalls 175 in the through-hole 153 of the fixed engaging device base 150. The purpose of the taper is to create a friction fit between the engaging device tag 160 and the engaging hole 401 in the bone implant 400. The engaging device tag 160 is inserted into, and preferably permanently affixed to, the through-hole 153 of the fixed engaging device base 150.

One or more grooves or slots 163 can be machined into the distal end 162 of the engaging device tag 160, thereby creating two or more cantilevered, opposing tag members 164, 165. This slot 163 can be formed in the length or width, or both, of the tapered tag distal end 162. In the preferred embodiment shown in FIG. 18, the engaging device tag 160 has two perpendicular slots 163 therein. By creating tag members that oppose each other, the slots 163 provide spring force between the tag members. This spring force aids in providing a friction fit when the engaging device tag 160 is inserted into the engaging hole 401 in the bone implant 400. In addition, the slots 163 allow for depth variability related to the depth with which the engaging device tag 160 can be inserted into the engaging hole 401. In general, the longer or deeper the slots 163, the deeper the engaging device tag 160 may be inserted into the engaging hole 401. The combination of the locking taper and the slots 163 allows and provides for a good friction fit when the engaging device tag 160 is press fitted into the engaging hole 401 in the bone implant 400.

Figure 21:
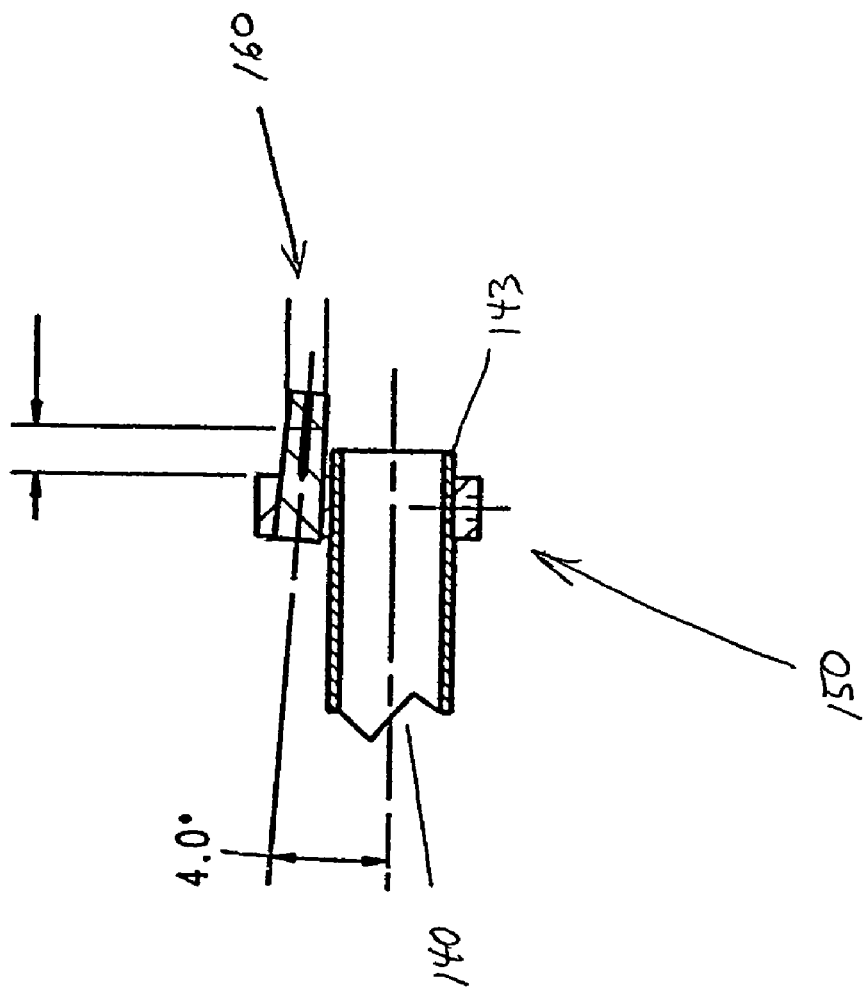
FIG. 21 is a detail elevation view of the distal end of the fixed cannula and engaging device according to a preferred embodiment of the present invention.

FIG. 21 shows that, ideally, the engaging device tag 160 is fixed to the distal end 143 of the cannula 140 so that the longitudinal centroidal axis of the engaging device tag 160 (that is, the longitudinal axis that intersects the centroid of the engaging device tag 160) is at an angle of approximately 4° from the longitudinal axis of the cannula 140. This matches the preferred 4° medial-lateral angle of inclination of the longitudinal axis of the fastener through-holes 402 described above. Likewise, the cephalad-caudal angle at which the cannula 140 is inserted into the fixed engaging device base 150 can vary, and is preferably situated at approximately a 10° cephalad-caudal arrangement. This preferred caudal-cephalad divergence tends to put the bone implant 400 in tension when implanted. Typically, the engaging device tag 160 is made from the same materials as is the fixed engaging device base 150.

FIGS. 22, 23, and 24 show how the fixed guide 100 is releasably attached to the bone implant 400. The distance from the centroidal axis of the through-hole 153 to the axis of the annular cylindrical eye 154 in the fixed engaging device base 150 corresponds to the distance from the centroidal axis of the engaging hole 401 in the bone implant 400 to the centroidal axis of the fastener through-hole 402. When mounted at the distal end of the cannula 140, the fixed engaging device base 150 assembly allows the instrument guide 10 to be press fitted into the engaging hole 401 in the bone implant 400. Thus, as shown in FIGS. 22, 23, and 24, when the engaging device tag 160 is inserted into engaging hole 401 in the bone implant 400, a friction fit is made between the engaging device tag 160 and the engaging hole 401. This aligns the cannula 140 to rest on the desired fastener through-hole 402. This in turn allows the instrument guide 10 to temporarily but securely hold the bone implant 400 in the desired relationship to the bone. The fixed engaging device base 150 is typically made from the same materials as is the cannula 140. With this arrangement, the surgeon may easily, removably attach the fixed guide 100 to the bone implant 400 to facilitate holding the bone implant 400 on the desired bones and simultaneously providing an opening through which numerous operative techniques may be employed at a correct orientation with respect to the bone implant 400.

Variable Guide 200

FIG. 25 depicts, in general, a variable guide 200. As can be seen, the variable embodiment is quite similar to the fixed embodiment described above. The differences lie in the design of the variable engaging device base 250 and the variable cannula 240.

FIG. 26 depicts a variable cannula 240 that likewise comprises a proximal end 241, a distal end 243, an outer cannula surface 242 and an inner cannula surface 244. It can be seen that the distal end 243 of the variable cannula 240 is a modification of the distal end 143 of the fixed cannula 140 (see FIG. 7). In particular, the variable cannula 240 includes a portion of a spheroidal ball 247 located at the distal end 243 adjacent a reduced collar 249. Stated alternatively, the portion of spheroidal ball 247 is a convex partially spheroidal section. The outside diameter of the spheroidal ball 247 is preferably slightly less than the outside diameter of the outer cannula surface 242. The spheroidal ball 247 mates with a spheroidal undercut 258 in the variable engaging device base 250 (FIG. 27), creating a type of ball and socket design that allows variability of the angle of entry of the bone fixation screw. The reduced collar 249 fits inside an annular cylindrical eye 254, and the spheroidal ball 247 allows rotation about the longitudinal axis of the cannula 240 shaft. As with the fixed cannula 140, the variable cannula 240 may be made from any material suitable for use in medical procedures, including but not limited to stainless steel, titanium, titanium alloys, and so forth.

As stated, the instrument guide 10 can have either a fixed engaging device base 150 or a variable engaging device base 250. FIGS. 25 through 35 generally depict a preferred embodiment of the variable instrument.

Figure 27:
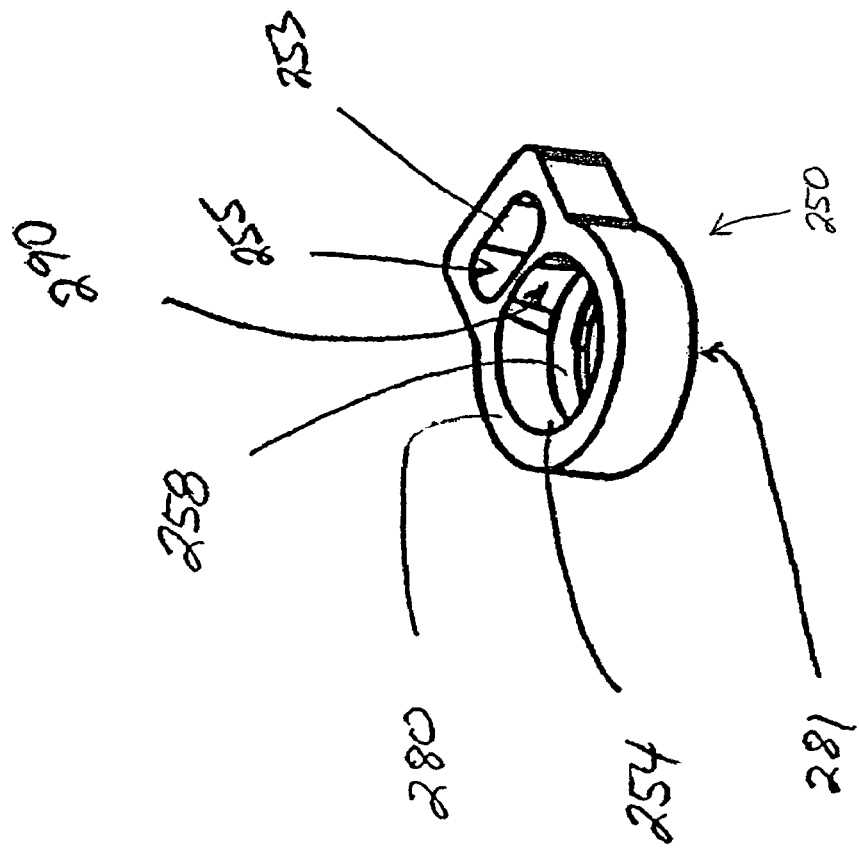
FIG. 27 is a perspective view of a variable engaging device base according to a preferred embodiment of the present invention.
Figure 30:
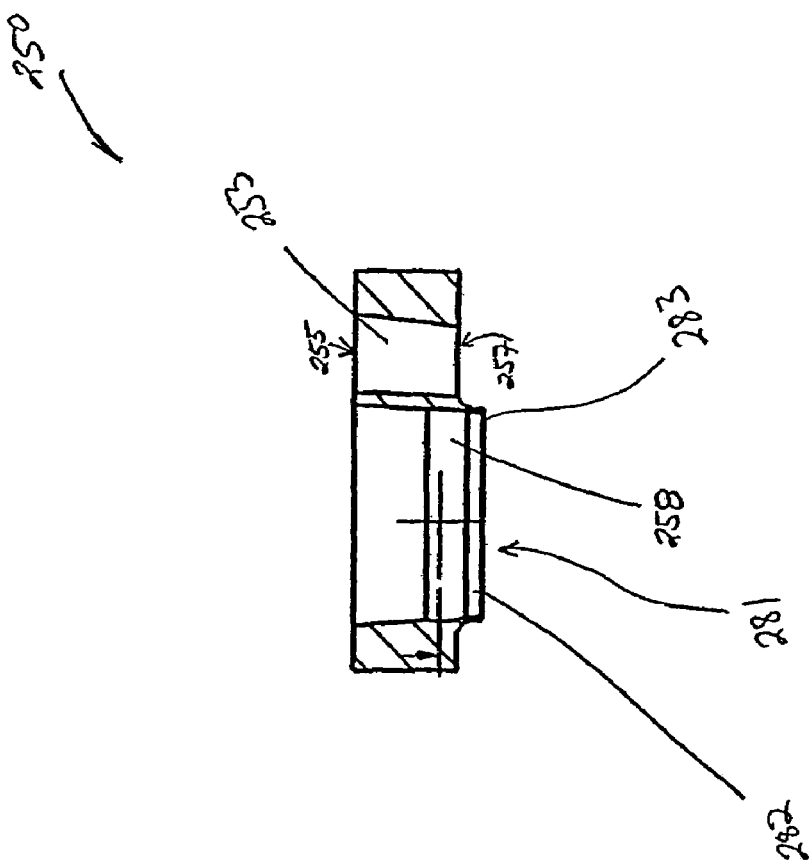
FIG. 30 is a cross-section view of the variable engaging device base of FIG. 27, taken at Section A-A of FIG. 29.

FIG. 27 is a perspective view of a variable engaging device base 250. In general, the variable engaging device base 250 is very similar to the fixed engaging device base 150, in that it has a generally annular cylindrical eye 254 at a first end thereof and a through-hole 253 at a second end thereof. The variable engaging device base 250 has an upper surface 280 and a lower surface 281. The annular cylindrical eye 254 has an entrance 252 and an exit 256. Likewise, the through-hole 253 has an entrance 255 and an exit 257.

Figure 29:
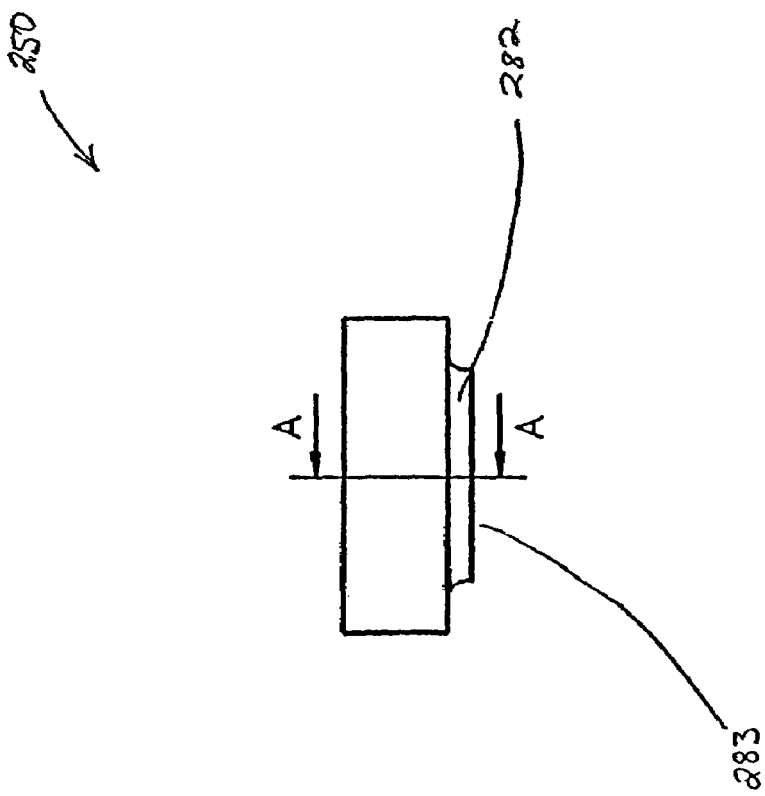
FIG. 29 is a front elevation view of the variable engaging device base of FIG. 27.
Figure 32:
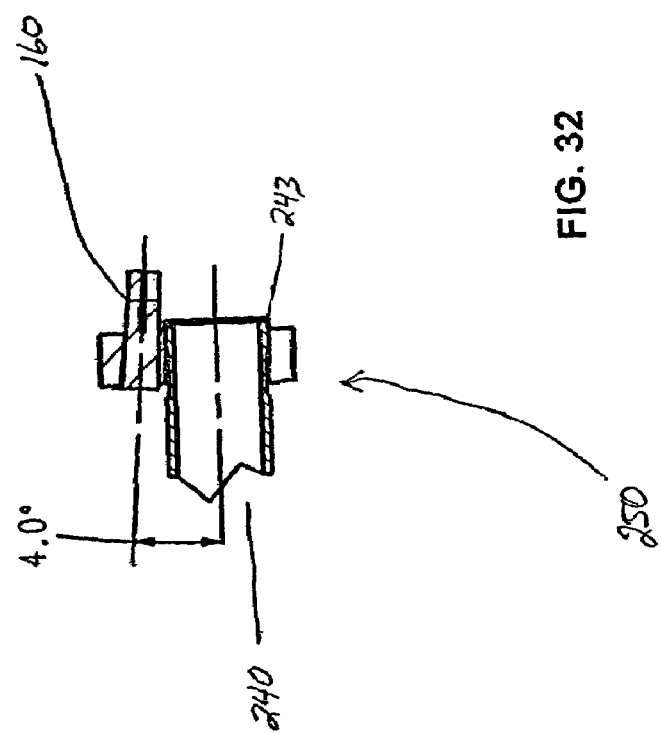
FIG. 32 is a detail view of the distal end of the variable cannula and variable engaging device of FIG. 31.

At one end of the annular cylindrical eye 254 is a spheroidal undercut 258 that mates with the spheroidal ball 247 at the distal end 243 of the variable cannula 240. This mating arrangement creates a ball and socket design that allows variability at angles ranging from approximately 1° to approximately 20° cone angle about the spheroidal center. The spheroidal undercut 258 can best be seen in FIG. 30. Additionally, the lower surface 281 of the variable engaging device base 250 preferably has a reduced diameter section 282 radiused from the lower surface 281 in order to create a lip 283 at the lower surface, as best shown in FIG. 29. This lip 283 fits into the fastener through-hole 402 in the bone implant 400 so that the annular cylindrical eye 254 sits on a flat diameter of the fastener through-hole 402 of the bone implant 400. As with the fixed engaging device base 150, the variable engaging device base 250 is preferably affixed (via adhesives, welding, and other standard fixation techniques) to the distal end 243 of the variable cannula 240, as is best shown in FIGS. 31 and 32.

Figure 28:
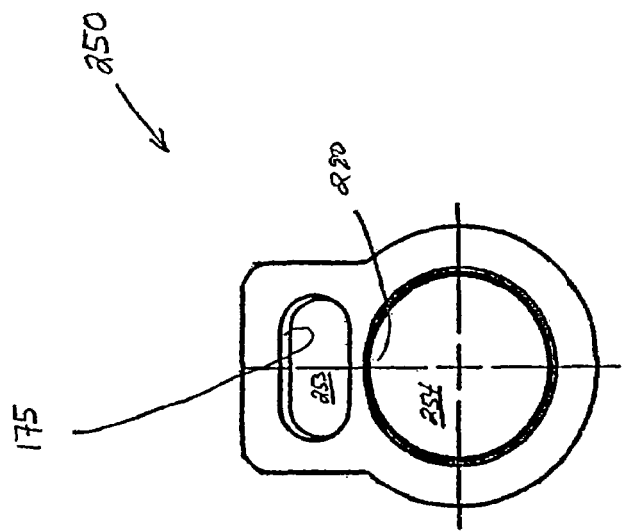
FIG. 28 is a top view of the variable engaging device base of FIG. 27.

FIGS. 27 and 28 depict additional elements of the preferred embodiment of the variable guide 200. In particular, a stop mechanism 290 is preferably located within the annular cylindrical eye 254. In the preferred embodiment, the stop mechanism 290 comprises a raised portion 291 as shown in FIG. 27. It should be readily observed that the stop mechanism 290, if present at all, can be located anywhere along the circumference of the annular cylindrical eye 254. Ideally, since bone screws usable for implants according to the present invention are not desired to be inserted at angles in the medial-lateral plane that diverge after the screw exits the bone implant, the stop mechanism 290 preferably is designed to prevent movement of the longitudinal axis of the fastener through-hole 402 past vertical (0°) in the medial direction.

Referring again to FIGS. 27 and 28, as with the fixed engaging device base 150, the through-hole 253 of variable engaging device base 250 can take many shapes, but preferably is generally ovoidal in section. The through-hole 253 similarly receives a mating engaging device tag 160, generally as described above in the context of the fixed instrument guide 10 (see FIGS. 18, 19, and 20).

The engaging device tag 160 is inserted into, and preferably affixed to, the internal surface of the through-hole 253 of the variable engaging device base 250. Again, the angle of inclination from the longitudinal axis of the through-hole 253 can vary, but is preferably approximately 4°, as shown in FIG. 32. This provides a preferred medial-lateral angle of approximately 4° to coincide with the preferred angle of the offset of the implant.

Figure 34:
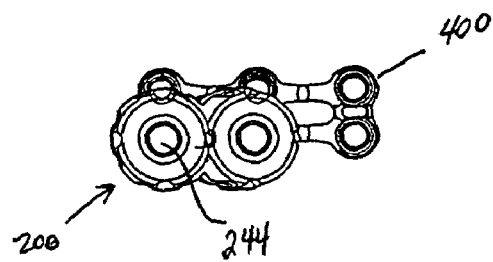
FIG. 34 is a top view of the fixed guide of FIG. 33 attached to a bone plate.
Figure 33:
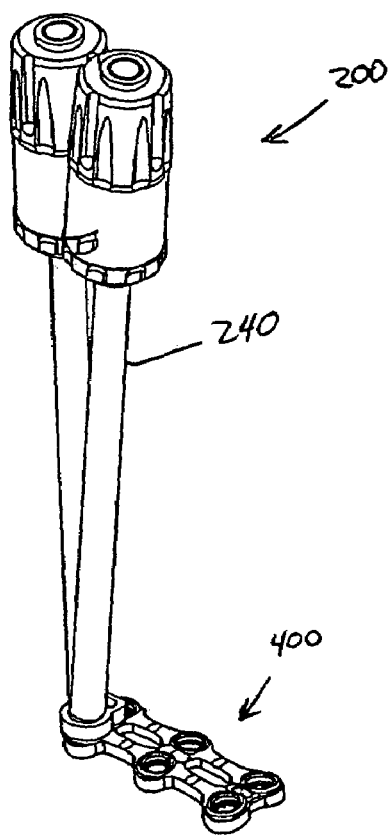
FIG. 33 is a perspective view of the variable guide attached to the bone implant according to a preferred embodiment of the present invention.
Figure 35:
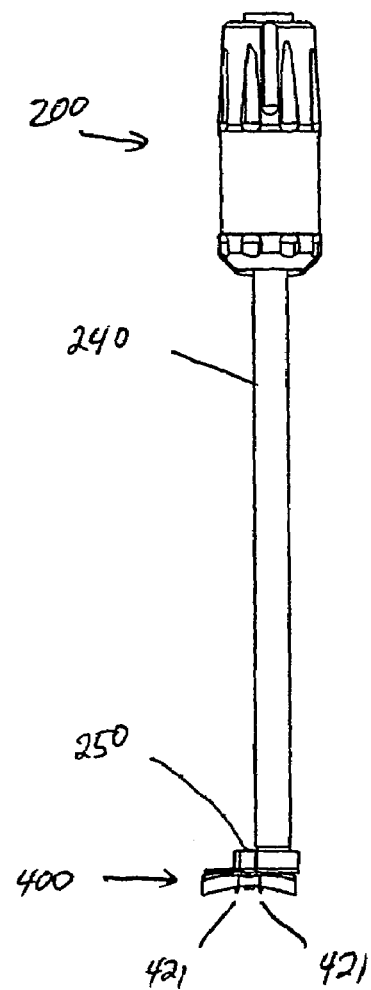
FIG. 35 is a caudal end view of the fixed guide of FIG. 33 attached to a bone plate.
Figure 36:
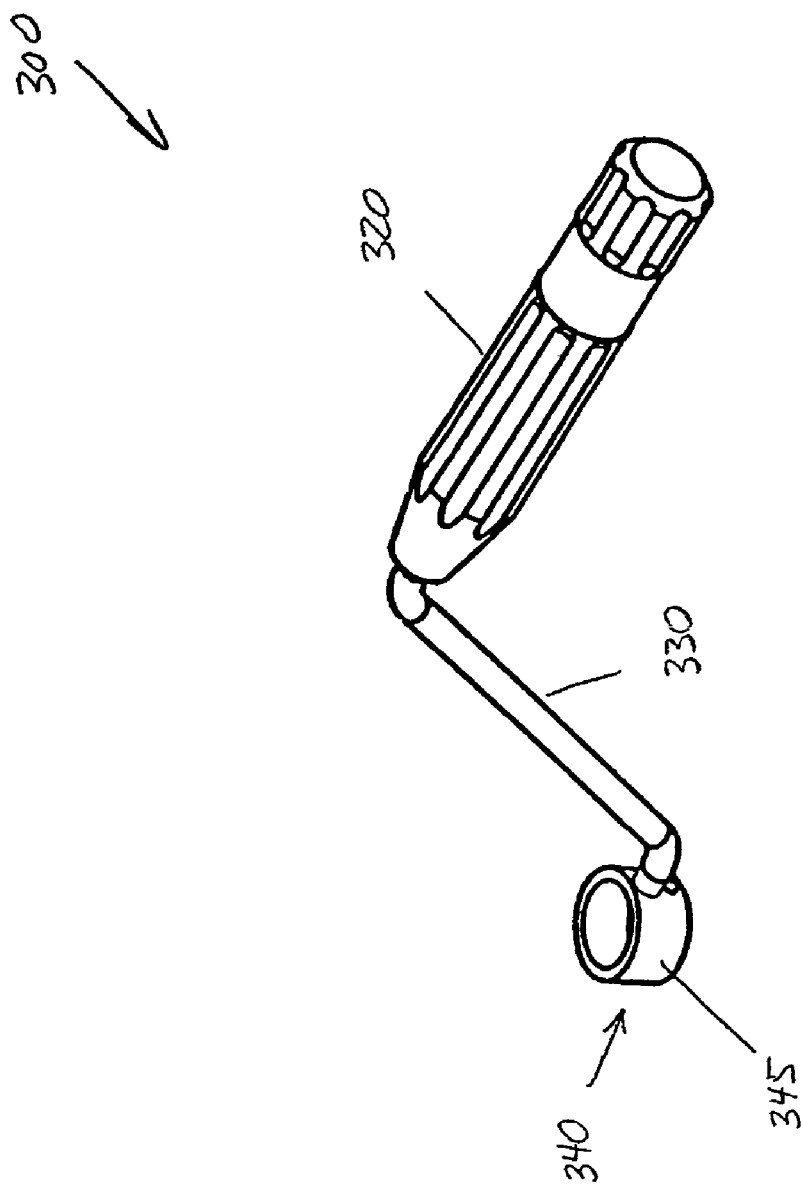
FIG. 36 is a perspective view of a guide extension according to an embodiment of the present invention.
Figure 37:
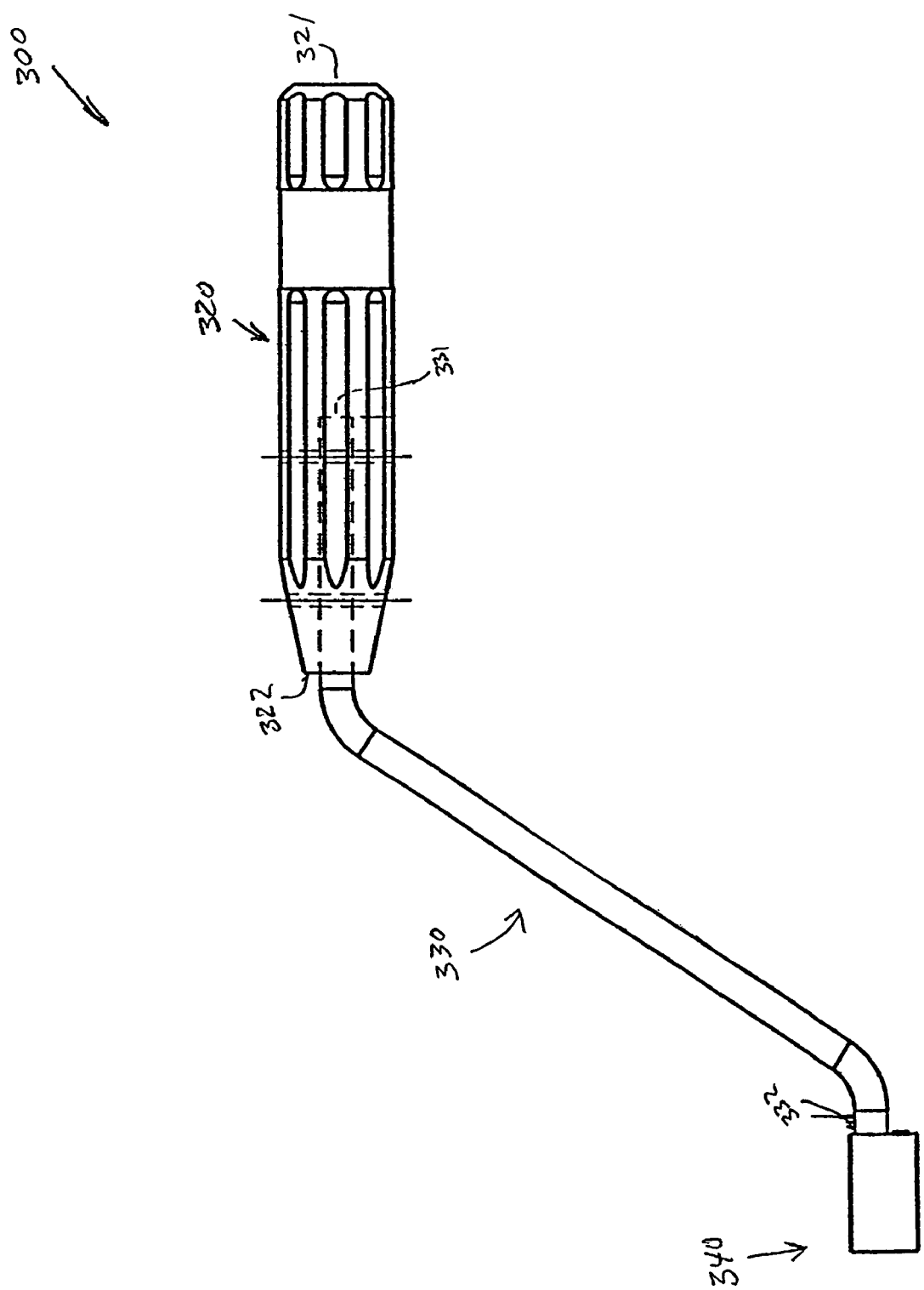
FIG. 37 is a side elevation view of the guide extension of FIG. 36.

FIGS. 33, 34, and 35, show a variable guide 200 attached to the bone implant 400 at two different angles of inclination. The manner of using the variable guide 200 is akin to that described for the fixed guide 100. Namely, the user inserts the engaging device tag 160 into engaging hole 401 in the bone implant 400. This creates a friction fit between the engaging device tag 160 and the engaging hole 401, thus releasably securing the variable guide 200 to the bone implant 400. The cannula 240 may then rest on the desired fastener through-hole 402 in any of a number of desired angles of inclination about the spheroidal center of the spheroidal ball 247. After the user has performed the desired operative techniques through the cannula 240, the variable guide 200 may be easily removed from the bone implant 400 by applying a slight tensile force thereto.

Guide Extension 300

FIGS. 36 through 42 depict an optional guide extension 300. The guide extension 300 facilitates surgeons who prefer holding a bone implant 400 at an offset from the area in which the medical instruments are inserted. Generally, the guide extension 300 comprises an extension handle 320, a rod 330, and a holder subassembly 340 for releasably fixing the guide extension 300 to the guide handle 20 described above. The extension handle 320 comprises a proximal end 321 and a distal end 322. Likewise, the rod 330 comprises a proximal end 331 and a distal end 332. As with the guide handle 20, the guide extension 300 is typically of generalized cylindrical shape made from any of a number of materials, such as high temperature plastic (Radel), anodized aluminum, and so forth. In addition, the guide extension 300 may be ergonomic or non-ergonomic in design and can have a plurality of machined grooves or other various appurtenances designed to improve gripping. The distal end 322 of the extension handle 320 is designed to receive the proximal end 331 of the rod 330. The proximal end 331 of the rod 330 is inserted into, and fixed to, the distal end 322 of the extension handle 320. The distal end 332 of the rod 330 is designed to receive the holder subassembly 340 described below. The rod 330 can be of varying shape and size, depending in part on the size of the work area and the preference of the surgeon as to the desired distance and height of the guide extension 300. In the preferred embodiment, rod 330 is a bent rod.

Figure 39:
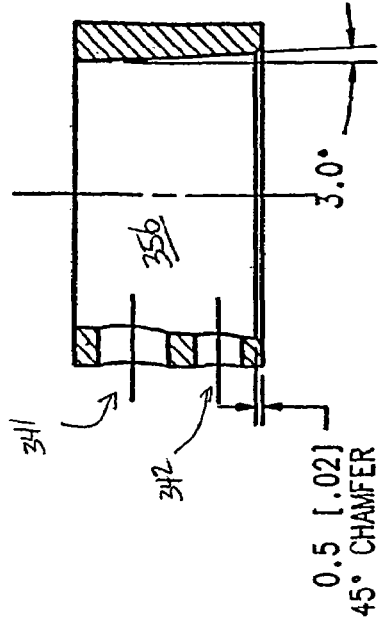
FIG. 39 is a partial cross-sectional view of the collar of FIG. 38.
Figure 41:
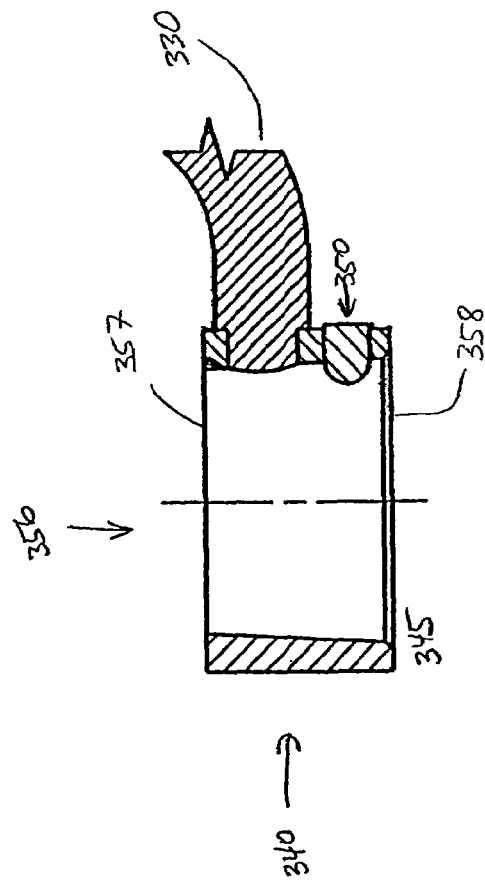
FIG. 41 is a cross-section view of the collar according to an embodiment of the present invention, showing in partial section the distal end of the rod of FIG. 36 and the hemispherical surface of the holding pin of FIG. 40.
Figure 38:
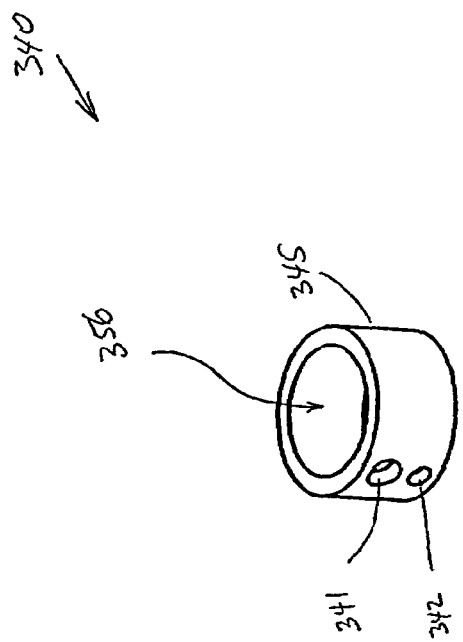
FIG. 38 is a perspective view of the collar according to an embodiment of the present invention.
Figure 40:
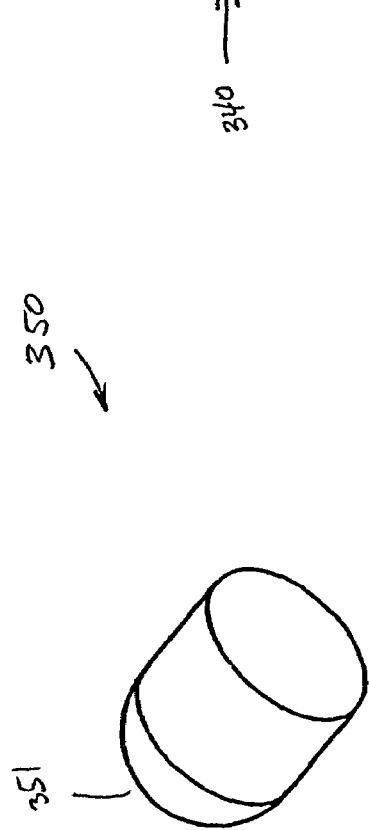
FIG. 40 is a perspective view of a holding pin according to an embodiment of the present invention.
Figure 42:
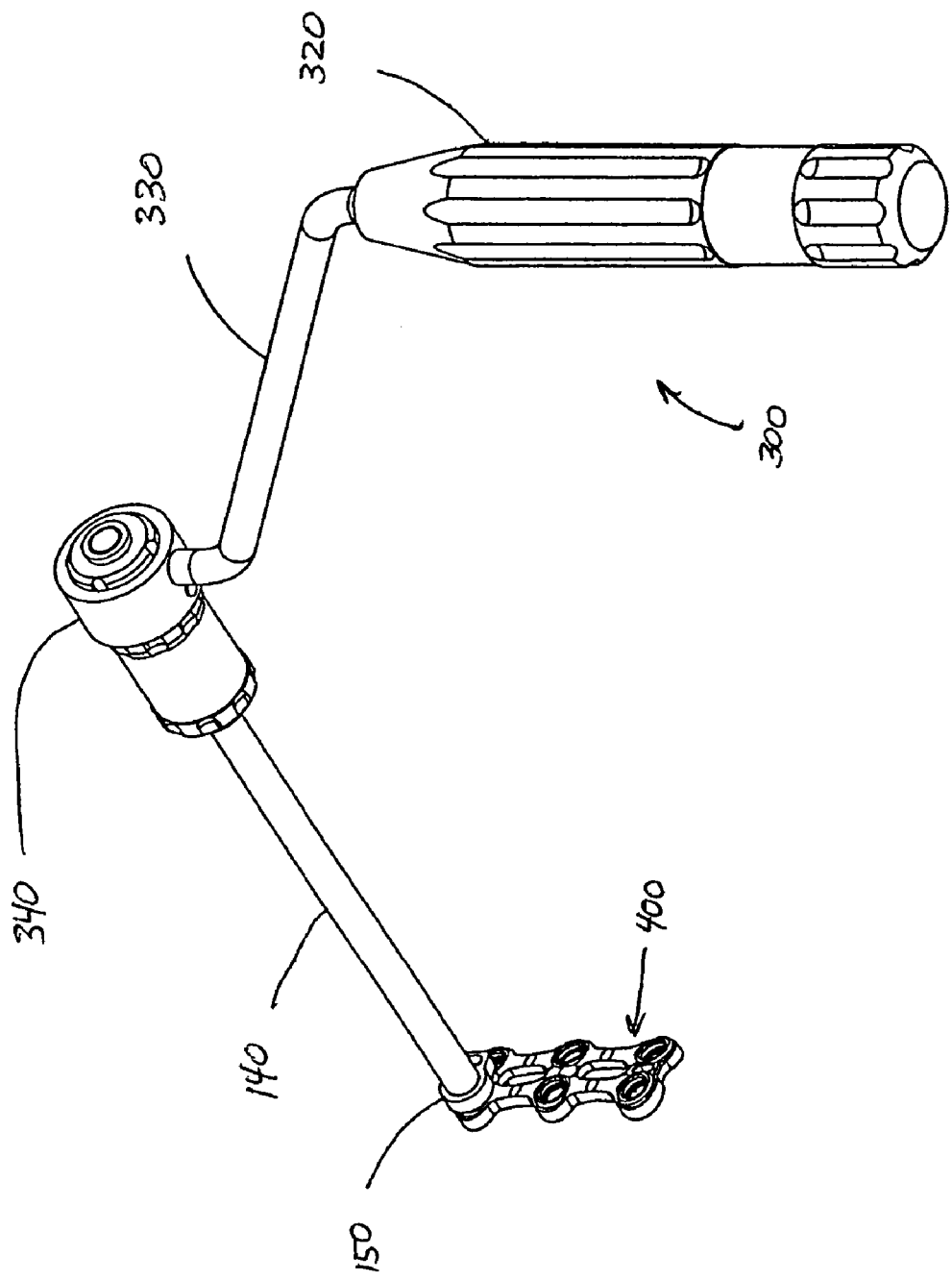
FIG. 42 is a perspective view of the guide extension of FIG. 36 attached to the fixed guide of FIG. 2 and the bone implant of FIG. 8.

The holder subassembly 340 is best shown in FIGS. 38 and 39. It can be seen that the holder subassembly 340 comprises a generalized open right circular cylinder, or collar 345, defining an opening 356 therethrough having an upper end 357 and a lower end 358, and having a first through-hole 341 and a second through-hole 342 in its side wall 343. Preferably, the opening 356 of the holder subassembly 340 is tapered such that lower end 358 is of slightly greater diameter than upper end 357. This allows the guide extension 300 to easily fit over and releasably attach to the guide handle 20. The opening 356 in the collar 345 comprises a tapered surface ranging from approximately 0° to approximately 20°. The preferred tapered surface is approximately 3°, as shown in FIG. 39. The first through-hole 341 receives the distal end 332 of the rod 330. The second through-hole 342 receives a holding pin 350, depicted in FIG. 40, and generally comprises a regular right cylinder having on one end a hemispherical head 351. The hemispherical head 351 protrudes through the second through-hole 342 and into the opening of the collar 345 as shown in FIG. 41. The hemispherical head 351 interacts with one of the slots 25 that is machined into the guide handle 20 as best shown in FIG. 42. In this manner, the guide extension 300 may be releasably locked to the guide handle 20. The holding pin 350 provides sufficient locking force to releasably secure the guide extension 300 to the guide handle 20. Typically, the holder subassembly 340 is made of the same materials as that of the cannula 140. When used in the surgical context, preferred materials include stainless steel, titanium, alloys thereof, and so forth.

Variable Locking Guide 500

FIGS. 43 through 50 depict a variable locking guide 500 embodiment of the variable guide 200 wherein the cannula 240 can be locked in a given orientation with respect to the centroidal axis of the fastener through-hole 402. This allows the surgeon to choose an angle for the fastener 403 and then lock the variable locking guide 500 so that all operative techniques (for example, puncturing, drilling, tapping, verifying hole depth, and fixating a fastener therein) in the fastener through-hole 402 are carried out at the same angle. This reduces the likelihood of thread stripping and misalignment, and improves the mechanical properties of the union between the fastener 403 and the bone implant 400.

Figure 43:
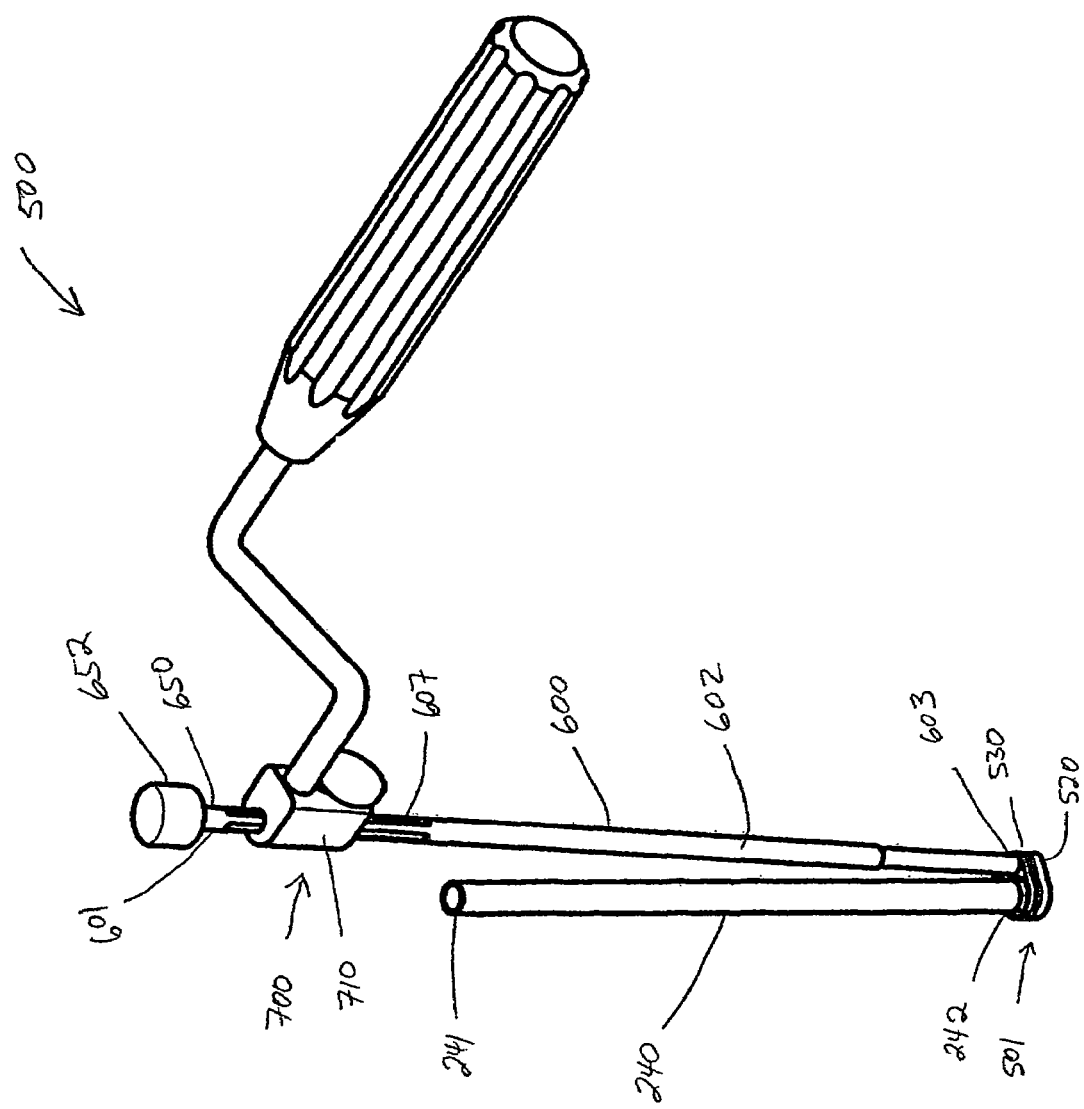
FIG. 43 is a perspective view of a variable locking instrument guide according to a preferred embodiment.

In general, as shown in FIG. 43, this embodiment employs the variable cannula 240, the engaging device tag 160, the extension handle 320, and the rod 330 described above, in addition to the following elements: a modified engaging device base 501; a draw rod cannula 600; a draw rod 650; and an optional extension handle bulkhead 700.

Figure 44:
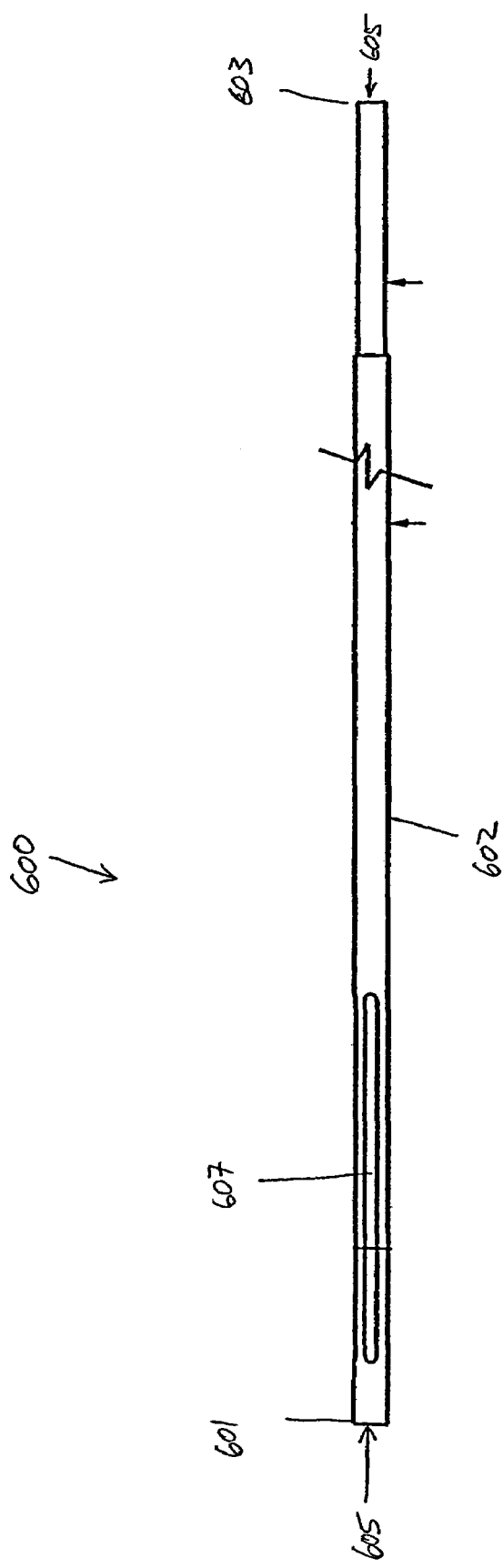
FIG. 44 is a longitudinal elevation view of a draw rod cannula according to a preferred embodiment of the present invention.

FIG. 44 depicts the draw rod cannula 600. The draw rod cannula 600 comprises a proximal end 601 and a distal end 603, an outer draw rod cannula surface 602 and an inner draw rod cannula surface 604 defining an annular cylindrical opening 605 therethrough. In applications that have small operative space, typically using small bone implants, the diameter of the outer draw rod cannula surface 602 is smaller at the distal end 603 than at the proximal end 601. One or more longitudinal depressions 607 can be located on the outer draw rod cannula surface 602. These longitudinal depressions 607 can be spaced about the outer draw rod cannula surface 602 in many arrangements, and are designed to receive a spring biased detent 751 (described below) in the extension handle bulkhead 700 (described below). The length of the longitudinal depressions 607 provide variability in the distance the extension handle 320 is from the distal end 603 of the draw rod cannula 600 (that is, in the surgical region). In the preferred embodiment, the longitudinal depressions 607 are spaced at 0°, 90°, and 180° about the circumference of the outer draw rod cannula surface 602. This spacing provides the surgeon with convenient reference points for the orientation of the variable locking guide 500.

Figure 45:
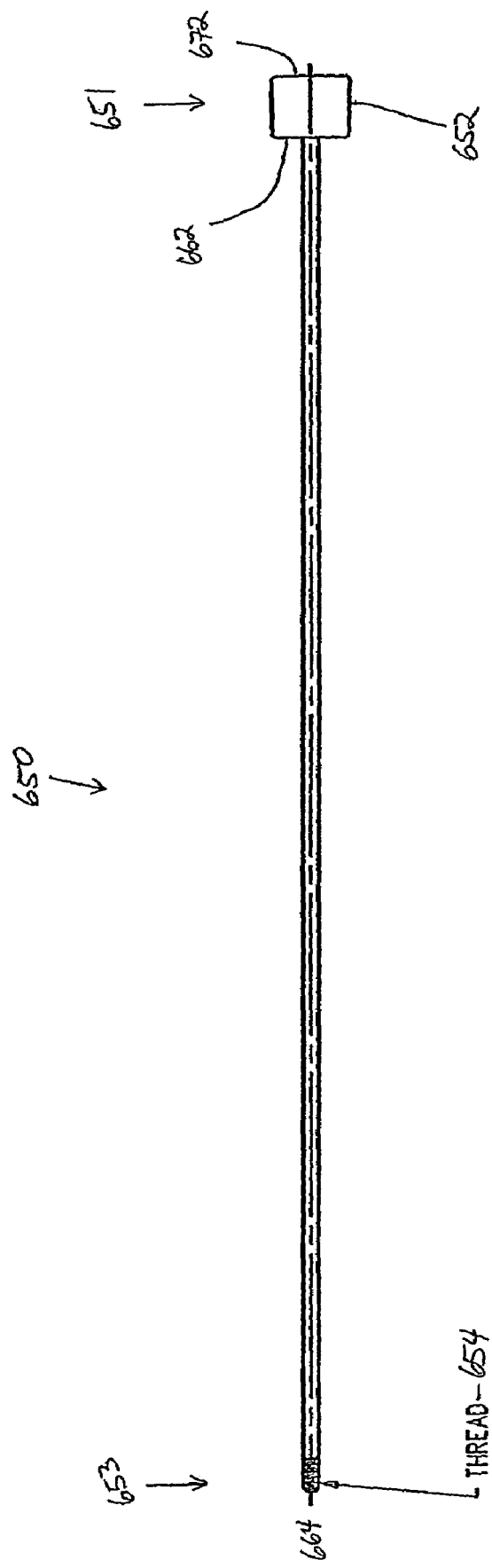
FIG. 45 is a longitudinal elevation view of a draw rod according to a preferred embodiment of the present invention.

FIG. 45 depicts a draw rod 650 that comprises, generally, a substantially cylindrical rod having a rod diameter that is insertable into the draw rod cannula 600. The draw rod 650 comprises a proximal end 651 and a distal end 653. An enlarged head 652 (preferably a thumb screw) having a first surface 662 and a second surface 672 is attached to the proximal end 651 so as to provide a means for rotatably moving the draw rod 650 inside the draw rod cannula 600. A threaded portion 654 extends from the distal end 653 of the draw rod 650 and terminates at a tip 664. The threaded portion 654 engages a mating threaded portion located in the engaging device base 501 (described below). The overall length of the draw rod 650 depends on the length of the draw rod cannula 600. Specifically, the distance from the tip 664 to the first surface 662 is sufficient to allow threaded portion 654 to threadedly engage mating threaded portion in the engaging device base 501.

Figure 46:
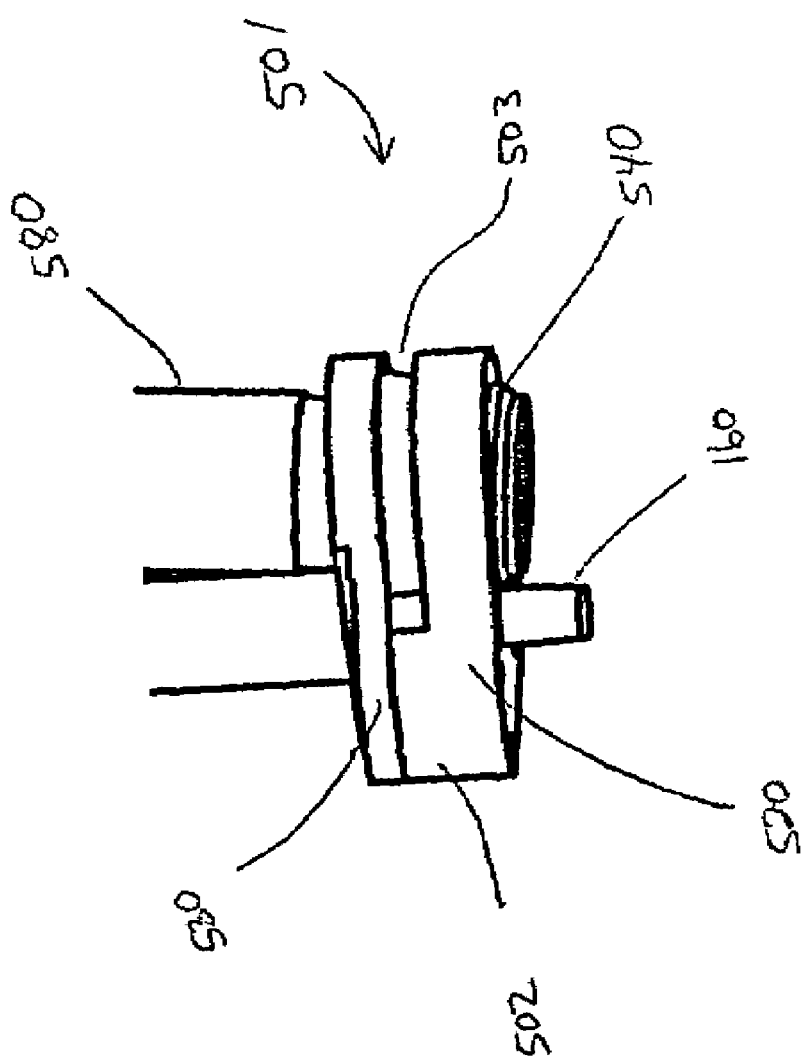
FIG. 46 is a perspective detail view of the distal end of the variable locking guide according to a preferred embodiment of the present invention showing a modified engaging device base.

FIG. 46 depicts the modified engaging device base 501 as it is attached to the distal end 243 of the variable cannula 240. Engaging device base 501 may comprise a single component or multiple components, depending on the size and geometric requirements of the surgical procedures and bone implant to be employed. In either event, the engaging device base 501, in use, comprises two opposing portions—base member bottom 520 and base member top 530 that are cantilevered about a fixed support section 502 that defines a gap 503 between the base member bottom 520 and base member top 530, best seen in FIG. 46.

Figure 47A:
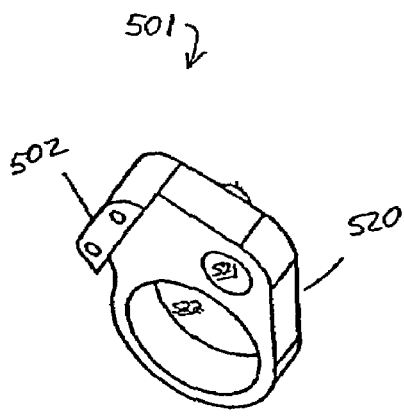
FIG. 47(a) is a perspective view of the engaging device base member bottom portion of FIG. 46.
Figure 47B:
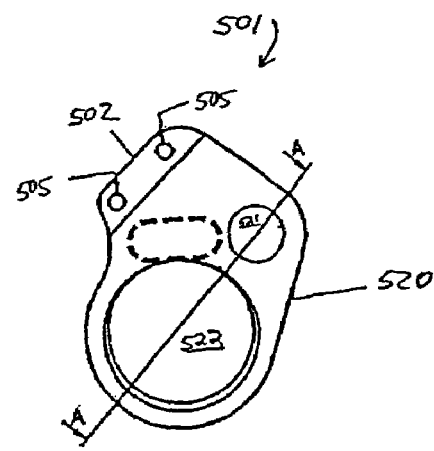
FIG. 47(b) is a top view of the engaging device base bottom portion of FIG. 47(a)
Figure 47C:
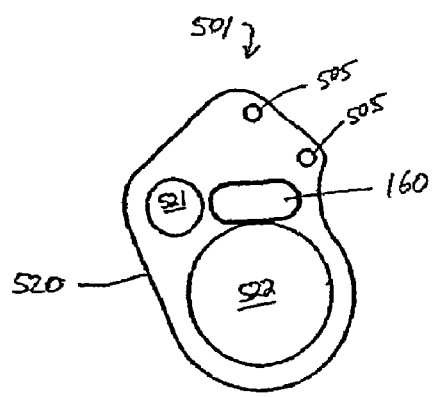
FIG. 47(c) is a bottom view of the engaging device base bottom portion of FIG. 47(a)
Figure 47D:
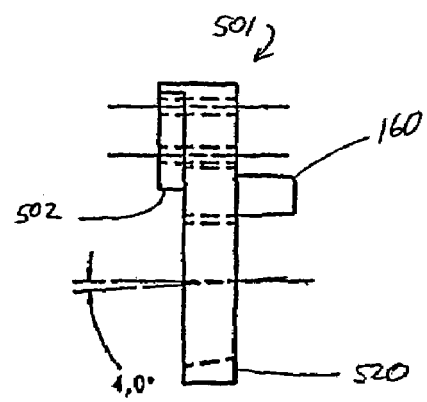
FIG. 47(d) is a side view of the engaging device base bottom portion of FIG. 47(a)
Figure 47E:
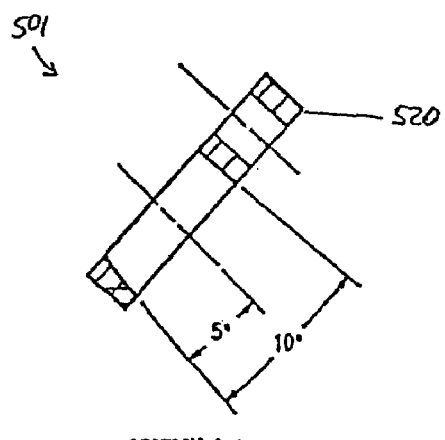
FIG. 47(e) is a cross-sectional view of the engaging device base member bottom portion taken at Section A-A of FIG. 47(b)

FIGS. 47(a)-(e) and 48 (a)-(d) depict the components of the modified engaging device base 501. In the preferred embodiment for cervical spine applications which have significant anatomical and operative space limitations, the engaging device base 501 comprises two separate components (base member bottom 520 and base member top 530) that are joined at one side at the fixed support section 502. As shown in FIG. 47(a), at least one of the base member bottom 520 or base member top 530 has a thickness at the fixed support section 502 that is greater than the thickness of the base member bottom 520 or base member top 530 elsewhere. The purpose for this is to provide the gap 503 (FIG. 46) between the base member bottom 520 and base member top 530. In the preferred embodiment, during fabrication, the base member bottom 520 and base member top 530 are first held together by two pins 504, as shown in FIGS. 47(b) and 48(b). Pins 504 are inserted into pin holes 505 in both base member bottom 520 and base member top 530. Pin holes 505 are in coaxial alignment in both base member bottom 520 and base member top 530. Once held in place with pins 504, base member bottom 520 and base member top 530 are then welded together using techniques commonly known in the art for the materials used.

FIGS. 48(a)-(d) depict, in general, base member top 530 comprising a first through-hole 531 therein for receiving the draw rod cannula 600. Preferably the diameter of the first through-hole 531 is slightly greater than the diameter of the outer draw rod cannula surface 602 so that the draw rod cannula 600 can be inserted into, and fixedly attached to, the first through-hole 531. Preferably, as shown in FIG. 43, the draw rod cannula 600 is affixed to the base member top 530 so that the longitudinal axis of the draw rod cannula 600 is perpendicular to the top surface of the base member top 530, though various angles of inclination are possible, depending on the needs of the surgeon and the anatomic and geometric constraints involved with the bone implant.

Similarly, base member bottom 520 likewise has a first through-hole 521 that has its axis coincident with (i.e., coaxial) the axis of the first through-hole 531 in the base member top 530. This ensures that the through-holes 521 and 531 line up. First through-hole 521 is designed to threadedly receive the threaded portion 654 of the draw rod 650. As a result, in the preferred embodiment depicted in FIGS. 47(a) through 35(e), first through-hole 521 contains internal threads that receive the external threads at the distal end 653 of the draw rod 650. Therefore, in the preferred embodiment, the diameter of first through-hole 521 is less than the diameter of first through-hole 531.

Base member top 530 further comprises a second through-hole 532 (having an opening 533 at the top surface of the base member top 530 and an exit 534 at the bottom surface of the base member top 530) for receiving variable cannula 240. Second through-hole 532 can have its axis at varying angles of inclination to the top surface of the base member top 530, again depending on the size of the variable locking guide 500 employed. Larger devices according to the invention can utilize larger angles of inclination because more material is present in the components of the engaging device base 501. In the small cervical application of the preferred embodiment, the angle of inclination of the axis of the second through-hole 532 with respect to the top of the base member top 530 in a transverse plane intersecting the center of the through-hole 532 can vary from approximately 0° to approximately 20°, and is preferably approximately 4° to correspond to a preferred 4° medial-lateral angle of curvature of the bone implant 400. To facilitate the variable cannula 240-and the consequent varying angulation thereof with respect to the longitudinal axis of the center line of the second through-hole 532—the second through-hole 532 is tapered from the opening 533 to the exit, so that the opening 533 is larger than the exit 534. The taper is preferably a linear taper, and can vary from approximately 0° to approximately 20°, depending again on the intended use for the device.

Similarly, base member bottom 520 has a second through-hole 522 therein that has its centroidal axis coincident with the axis of the second through-hole 532 in the base member top 530, so that the axes of the through-holes 522 and 532 are coincident. Through-hole 522 has a geometry similar to that of through-hole 532 described above. In contrast, however, through-hole 522 receives a drill cannula bushing 540 that receives the distal end 243 of variable cannula 240.

FIGS. 49(a)-(d) depict a drill cannula bushing 540 comprising, generally, an annular cylinder 541 having an outer surface 542 and an inner surface 543 terminating at an upper ridge 544 and a lower ridge 545. In the preferred embodiment, the annular cylinder 541 is a split ring cylinder. The lower ridge 545 of annular cylinder 541 sits within the second through-hole 522 of base member bottom 520. The outer surface 542 of the drill cannula bushing 540 preferably has a taper that matches the taper of the inner surface of the second through-hole 522, which can vary between 0° and approximately 20°. In the preferred embodiment, the taper of the outer surface 542 of the drill cannula bushing 540 is approximately 5°.

The inner surface 543 likewise comprises a taper, but typically has a greater angle than does the outer surface 542. This is because the inner surface 543 receives the variable cannula 240 and determines the amount of angulation allowable for the variable cannula 240. Therefore, the maximum angle allowed by the materials and size of the engaging device base 501 will typically be utilized for the inner surface 543. In the preferred embodiment used for cervical applications, the inner surface 543 taper is approximately 10°. Near the lower ridge 545, the inner surface 543 further comprises a partially spheroidal concavity 546 that receives the portion of the spheroidal ball 247 at the distal end 243 of the variable cannula 240.

With the lower ridge 545 of the drill cannula bushing 540 residing in the second through-hole 522 in the base member bottom 520, the upper ridge 544 contacts the lower surface of the base member top 530. Specifically, the outer diameter of the upper ridge 544 is slightly greater than the diameter of the exit 534 of the second through-hole 532 in the base member top 530. Therefore, when assembled, the drill cannula bushing 540 is wedged between the lower surface of the base member top 530 and the tapered second through-hole 522 in the base member bottom 520.

With this arrangement the variable locking guide 500 can releasably lock the variable cannula 240 into a predetermined orientation so that the surgeon can perform all necessary operative implant techniques (for example, drilling, tapping, inserting screws, and so forth) at this predetermined orientation. Referring again to FIG. 43, the surgeon moves the variable cannula 240 into the desired orientation with respect to the bone implant 400 and inserts the draw rod 650 into draw rod cannula 600. Draw rod 650 passes through first through-hole 531 in base member top 530 and approaches first through-hole 521 in base member bottom 520. The surgeon begins rotating enlarged head 652 on draw rod 650 so that threaded portion 654 begins to engage mating threaded portion in first through-hole 521 in base member bottom 520. As the surgeon rotates enlarged head 652, the threaded portion 654 continues to progress farther into first through-hole 521. This in turn imparts a force on the first through-hole 521 in base member bottom 520 that tends to force base member bottom 520 and base member top 530 together, thus tending to close the gap 503 therebetween. Recall that the diameter of upper ridge 544 is slightly greater than the diameter of opening 533 in second through-hole 532 in base member top 530. As this force is imparted, it therefore imparts a compressive force on upper ridge 544 of the drill cannula bushing 540 in the second through-hole 522. As this occurs, the annular cylinder 541 tends to expand in the second through-hole 522, thus providing a compressive force in a substantially radial direction on the substantially spheroidal ball 247 at the distal end 243 of the variable cannula 240. This provides a slight locking force on the variable cannula 240 that effectively locks the variable cannula 240 in its predetermined orientation. The surgeon can then perform all necessary surgical techniques through the variable cannula 240 at this, or any other, orientation. To disengage the lock, the surgeon simply rotates the enlarged head 652 in the opposite direction, thus disengaging the threaded section 654 from second through-hole 522. This removes the compressive force on the drill cannula bushing 540, and allows the gap 503 to expand to its normal, at rest position. In this manner, the surgeon can select many angles of orientation for a bone implant fastener 403.

It can be seen that the combination of the fixed support section 502 and the gap 503 between base member bottom 520 and base member top 530 provide the mechanism for imparting the necessary locking force on the drill cannula bushing 540 that locks the variable cannula 240 into place. In effect, a fulcrum is created against which the threaded portion 654 acts. The fixed support section 501 serves to bias the gap 503 at a predetermined distance. The threaded portion 654 of the draw rod 650 then is used to reduce the gap 503, thereby creating a compressive force on the drill cannula bushing 540.

Figure 50A:
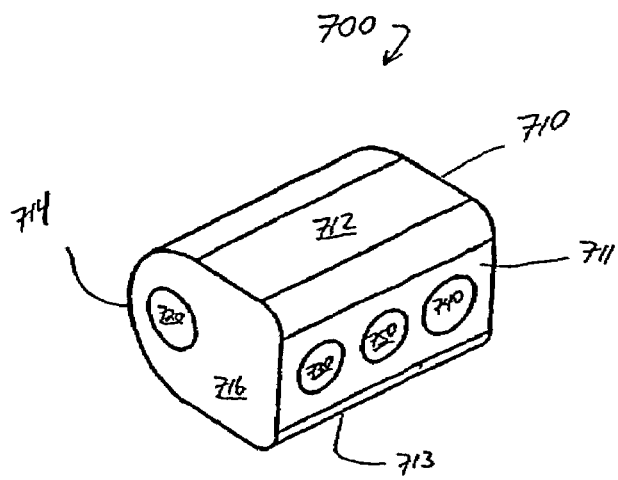
FIG. 50(a) is a perspective view of an extension handle bulkhead main body of the variable locking guide of FIG. 43.
Figure 50B:
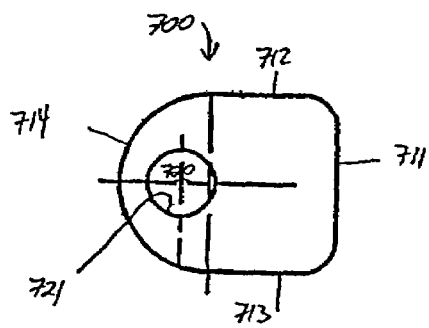
FIG. 50(b) is a top view of the extension handle bulkhead main body of FIG. 50(a)
Figure 50C:
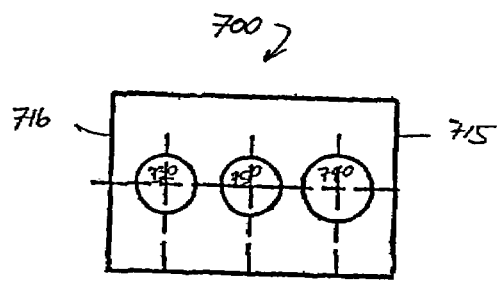
FIG. 50(c) is a side elevation view of the extension handle bulkhead main body of FIG. 50(a).
Figure 10:
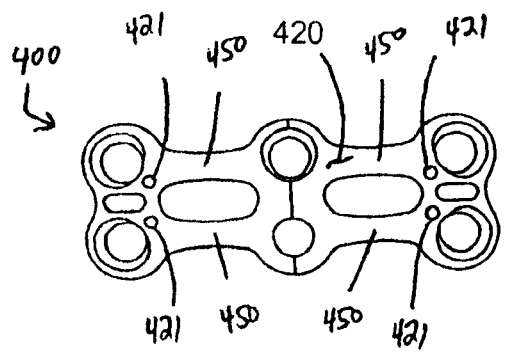
Figure 8:
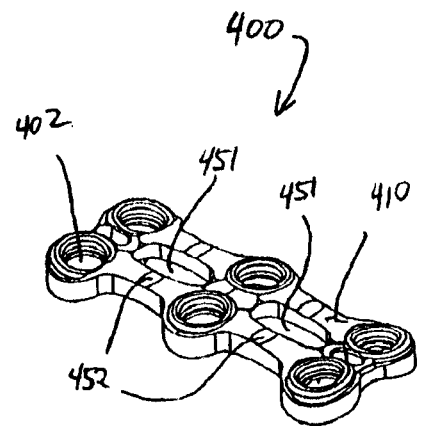
Figure 11:
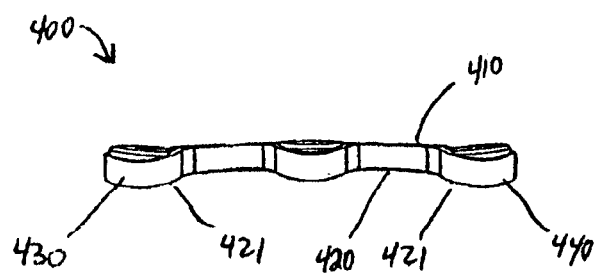
Figure 9:
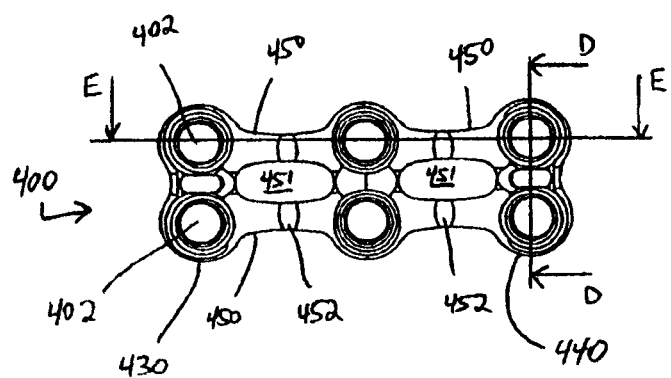
Figure 12:
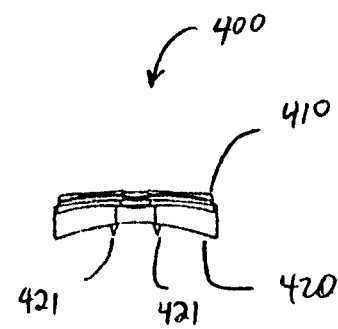
Figure 48A:
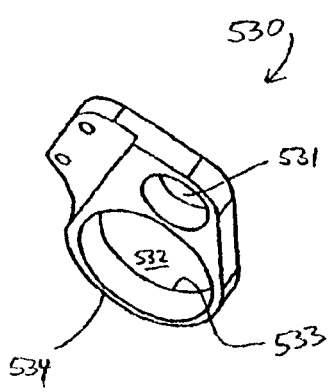
Figure 48B:
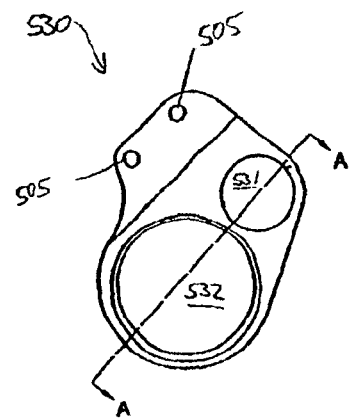
Figure 48C:
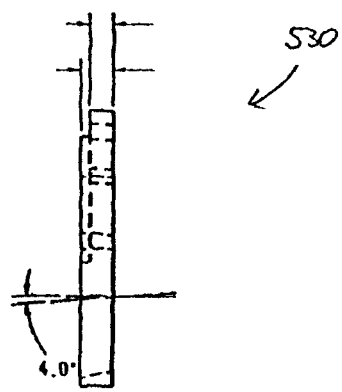
Figure 48D:
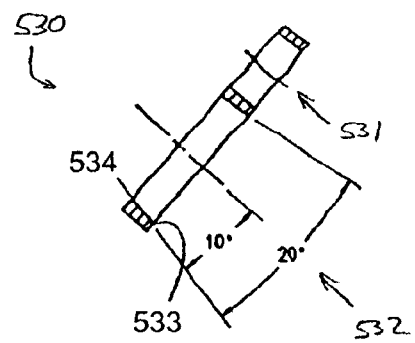

FIGS. 50(a) through (c) depict optional extension handle bulkhead 700 comprising a main body 710. Main body 710 can take many shapes, including as merely a few examples cylindrical, partially cylindrical, cubical, prismoidal, or any three-dimensional shape including polyhedron having a cross section that is n-tagonal (where n represents the number of sides of a regular polygon). In the preferred embodiment the main body 710 is substantially cylindrical having at least one longitudinal front face 711, two side faces 712 and 713 that are substantially perpendicular to said longitudinal front face 711, a longitudinal curvilinear back face 714 and an upper face 715 and a lower face 716. Both the upper face 715 and the lower face 716 lie in planes that intersect (preferably orthogonally) the longitudinal planes containing the longitudinal front face 711; the side faces 712, 713; and the back face 714.

Main body 710 further comprises a longitudinal through-hole 720 that extends through the main body 710 and upper and lower faces 715, 716. Preferably, longitudinal through-hole 720 further comprises an internal cylindrical surface 721 through which the draw rod cannula 600 is inserted. Main body 710 also comprises a first threaded transverse hole 730 that intersects the longitudinal through-hole 720 and penetrates one side of the internal cylindrical surface 721. First threaded transverse hole 730 threadedly receives a thumb screw 732, that has a tip 734 and an enlarged head 736. As the thumb screw 732 is threaded into the first threaded transverse hole 730, the tip 734 protrudes into the longitudinal through-hole 720. When the draw rod cannula 600 is resident within the longitudinal through-hole 720, thumb screw 732 engages the outer draw rod cannula surface 602. By continuing to thread the thumb screw 732 into the first threaded transverse hole 730, the thumb screw 732 progressively tightens against the outer draw rod cannula surface 602. This provides a locking force on the draw rod cannula 600 and effectively releasably locks the extension handle 320 in a given position about the draw rod cannula 600.

In addition, main body 710 preferably comprises an attachment mechanism for releasably attaching the rod 330 of the extension handle 320. The attachment mechanism can take many forms that are standard ways of attaching a rod to a solid object, including, but not limited to threaded connections whereby the rod 330 is threaded into the main body 710; slidable connections whereby the rod 330 incorporates a geometric section that slides into a mating geometric section on or in the main body 710; snap-fit connections; and so forth. In the preferred embodiment, main body 710 comprises a second threaded transverse hole 740 that, depending on preference, may or may not intersect the longitudinal through-hole 720 and penetrate one side of the internal cylindrical surface 721. Second threaded transverse hole 740 threadedly receives the distal end 332 of the rod 330 of the extension handle 320. In this manner the extension handle 320 is removably attached to the main body 710.

Main body 710 also comprises an engaging mechanism 750 that engages the longitudinal depressions 607 in the draw rod cannula 600. In the preferred embodiment, engaging mechanism 750 comprises a spring biased detent 751 that alternately slides from a protruding position to a retracted position. In the protruding position, spring biased detent 751 protrudes into the annular cylindrical opening 605 and engages longitudinal depression 607. In the retracted position, spring biased detent 751 is biased in a protruding position with a spring 752 that bears against a stop 753. The extension handle 320 can be rotated about the longitudinal axis of the draw rod cannula 600 so that a longitudinal depression 607 may be engaged by spring biased detent 751. Such detents are commonly known in the art and provide a convenient means of locating and indicating the relative orientations and positions of two or more objects with respect to each other by "popping into" a depression.

While there has been described and illustrated particular embodiments of an instrument guide and implant holder for releasably securing a guide to an implant, it will be apparent to those skilled in the art that variations and modifications are possible without deviating from the broad spirit and principle of the present invention, which shall be limited solely by the scope of the claims appended hereto.

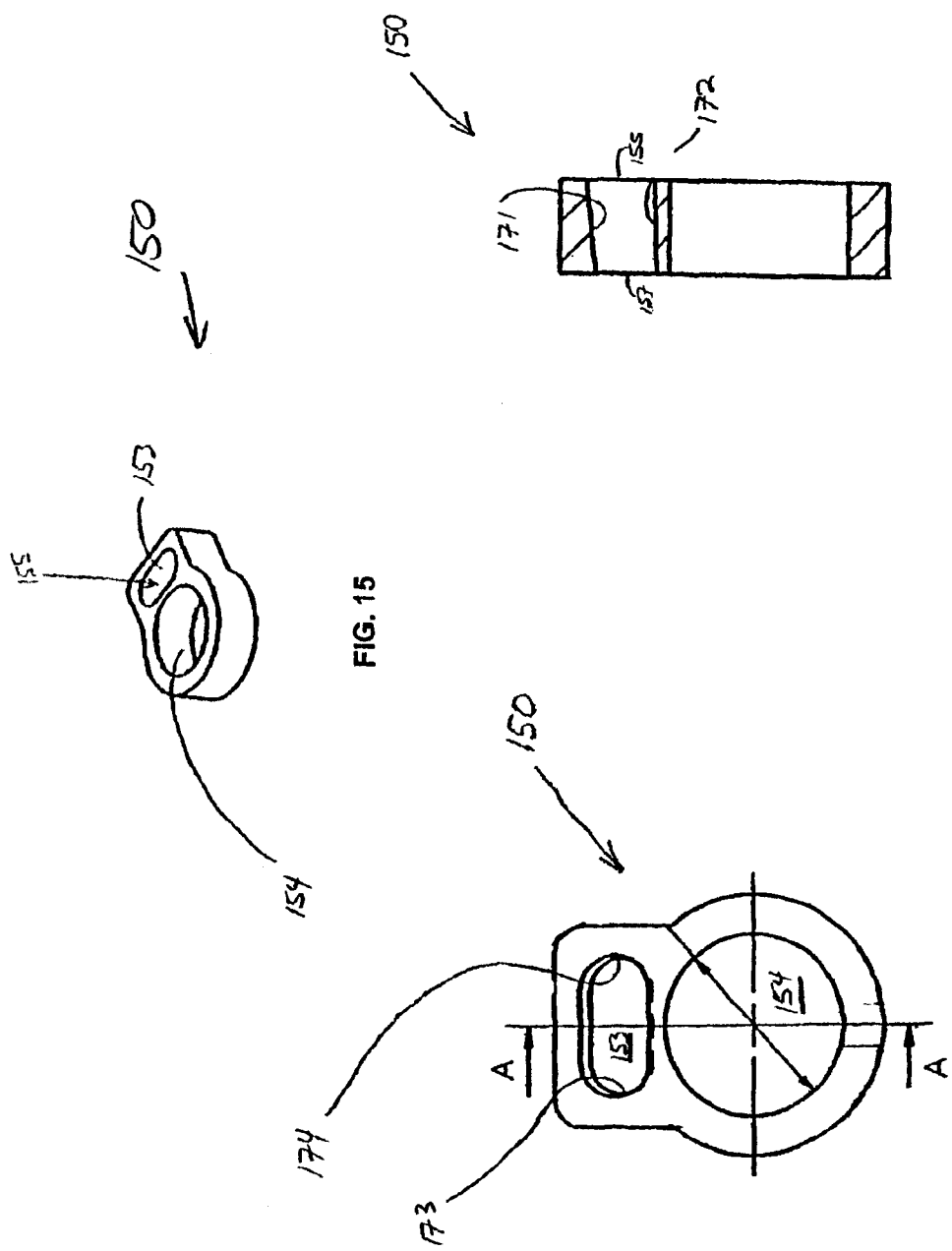

What is claimed is:

1. A variable locking instrument guide comprising:

a) a variable cannula having a proximal end and a distal end and having a partially spheroidal ball section having a spheroidal center at said distal end;

b) a draw rod having a proximal end and a distal end, said proximal end further comprising an enlarged head and said distal end further comprising a threaded portion;

c) a draw rod cannula for receiving said draw rod therethrough, wherein said draw rod cannula comprises a proximal end and a distal end;

d) an engaging device base further comprising a top portion and a bottom portion connected at a fixed support defining a gap therebetween, said engaging device base further comprising a first through-hole through said top portion and said bottom section for receiving a drill cannula bushing, said drill cannula bushing receiving therewithin said partially spheroidal ball section of said variable cannula, and said engaging device base further comprising a second through-hole through said top portion for receiving said distal end of said draw rod cannula, and a second threaded through-hole through said bottom portion that is coaxial with said second through-hole in said top portion, for threadedly receiving said threaded portion of said draw rod;

e) wherein in a first condition said variable cannula is rotatable about said spheroidal center; and f) in a second condition said draw rod engages said second threaded through-hole through said bottom portion releasably locking said variable cannula in a predetermined orientation about said spheroidal center.

2. The variable locking instrument guide of claim 1, further comprising a handle;
wherein said handle farther comprises an extension handle rod having a proximal end and a distal end wherein said distal end of said extension handle rod is received by said proximal end of said draw rod cannula.

3. The variable locking instrument guide of claim 2 wherein said distal end of said extension handle rod is received by an extension bulkhead that is removably attached to said proximal end of said draw rod cannula.

4. The variable locking instrument guide of claim 3 wherein said extension bulkhead further comprises a main body having a plurality of longitudinal faces and an upper face and a lower face, wherein a longitudinal through-hole extends through said upper face and said lower face for receiving said cannula draw rod, said longitudinal through-hole defining an open internal cylindrical surface within said main body.

5. The variable locking instrument guide of claim 4 wherein said main body further comprises a first threaded transverse hole that intersects said longitudinal throughhole and penetrates one side of said internal cylindrical surface and receives a threaded thumb screw.

6. The variable locking instrument guide of claim 5 wherein said main body further comprises a second threaded transverse hole that receives said distal end of said extension handle rod.

7. The variable locking instrument guide of claim 6 wherein said main body further comprises an engaging mechanism that is slidable from a protruding position wherein a spring biased detent engages longitudinal depressions in said draw rod cannula, and a retracted position wherein said spring biased detent does not engage said longitudinal depressions.

8. The variable locking instrument guide of claim 7 wherein said main body releasably and slidably engages said longitudinal depressions on an outer surface of said proximal end of said draw rod cannula.

9. The variable locking instrument guide of claim 1 wherein said engaging device base farther comprises a tag having a proximal end and a distal end wherein said proximal end of said tag is attached to said bottom portion of said engaging device base and wherein said distal end of said tag releasably engages a complementary hole in a bone implant.

10. The variable locking instrument guide of claim 1 wherein said first through-hole in said top portion has an opening at a top surface of said top portion and an exit at a bottom surface of said top portion wherein said opening has a diameter that is greater than a diameter of said exit.

11. The variable locking instrument guide of claim 10 wherein said drill cannula bushing has an outer circumferential surface taper and an inner circumferential surface taper.

12. The variable instrument guide of claim 11 wherein said outer circumferential taper is in the range of approximately 0 degrees to approximately 20 degrees.

13. The variable locking instrument guide of claim 12 wherein said outer circumferential taper is approximately 1 to 5 degrees.

14. The variable locking instrument guide of claim 11 wherein said inner circumferential taper is in the range of approximately 0 degrees to approximately 20 degrees.

15. The variable locking instrument guide of claim 14 wherein said inner circumferential taper is approximately 8 to 12 degrees.

16. The variable locking instrument guide of claim 11 wherein said drill cannula bushing is a split annular cylindrical member.

17. The variable locking instrument guide of claim 11 wherein said variable cannula is rotatable within said first through-hole about said longitudinal axis of said first through-hole at cone angles of orientation in the range of approximately 0 degrees to approximately 20 degrees.

18. The variable locking instrument guide of claim 1 wherein said first through-hole in said bottom portion has an opening at a top surface of said bottom portion and an exit at a bottom surface of said bottom portion wherein said opening has a diameter that is greater than a diameter of said exit.

19. The variable locking instrument guide of claim 18 wherein said drill cannula bushing has an outer circumferential surface that has a taper that matches a taper of said first through-hole in said bottom portion.

20. The variable locking instrument guide of claim 1 wherein said first through-hole in said top portion is located between said second through-hole and said fixed support.

21. The variable locking instrument guide of claim 20 wherein said first through-hole in said top portion is located between and colinear with said second through-hole and said fixed support.

22. The variable locking instrument guide of claim 1 wherein said draw rod provides a force on said bottom portion of said engaging device base that draws said bottom portion closer to said top portion.

23. The variable locking instrument guide of claim 1 wherein said draw rod compresses said drill cannula bushing.

24. A variable locking instrument guide comprising:

a) a variable cannula having a proximal end and a distal end and having a partially spheroidal ball section at said distal end;

b) a draw rod having a proximal end and a distal end, said proximal end further comprising an enlarged head and said distal end further comprising a threaded portion;

c) a draw rod cannula for receiving said draw rod therethrough, wherein said draw rod cannula comprises a proximal end and a distal end; and d) an engaging device base further comprising a top portion and a bottom portion connected at a fixed support defining a gap therebetween, said engaging device base further comprising a first through-hole through said top portion and said bottom portion for receiving a drill cannula bushing, said drill cannula bushing receiving therewithin said partially spheroidal ball section of said variable cannula, and said engaging device base further comprising a second through-hole through said top portion for receiving said distal end of said draw rod cannula, and a second through-hole through said bottom portion that is coaxial with said second through-hole in said top portion, for receiving said threaded portion of said draw rod;

e) wherein rotably moving said draw rod in said draw rod cannula engages said threaded portion of said draw rod with said second through-hole in said bottom portion, whereby further rotable engagement forces said bottom portion closer to said top portion, thereby reducing said gap therebetween and providing a compressive force on said drill cannula bushing, thus creating a locking force on said partially spheroidal ball at said distal end of said variable cannula, thus releasably locking said variable cannula in a predetermined orientation about the longitudinal axis of said first through-hole.

* * * * *

UNITED STATES PATENT AND TRADEMARK OFFICE
CERTIFICATE OF CORRECTION

| | |
|---|---|
| PATENT NO. | : 7,491,209 B2 |
| APPLICATION NO. | : 11/358982 |
| DATED | : February 17, 2009 |
| INVENTOR(S) | : Mueller et al. |

It is certified that error appears in the above-identified patent and that said Letters Patent is hereby corrected as shown below:

Replace drawing sheet 8 containing Figure 10 with the attached replacement drawing sheet containing Figure 10.

Replace drawing sheet 11 containing Figure 16 with the attached replacement drawing sheet containing Figure 16.

Figure 48A:
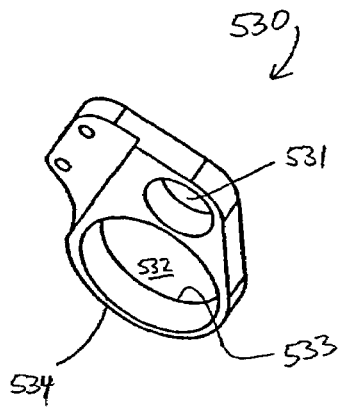
FIG. 48(a) is a perspective view of the engaging device base member top portion of FIG. 46.
Figure 48B:
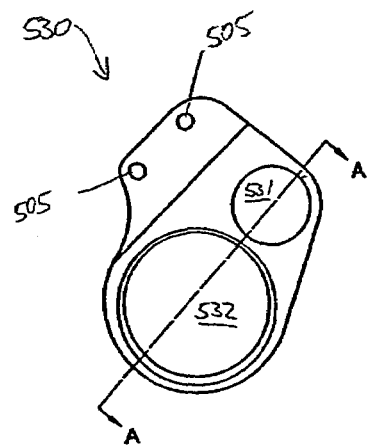
FIG. 48(b) is a top view of the engaging device base member top portion of FIG. 48(a)
Figure 48C:
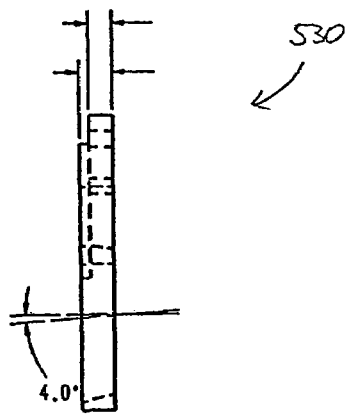
FIG. 48(c) is a side view of the engaging device base member top portion of FIG. 48(a)
Figure 48D:
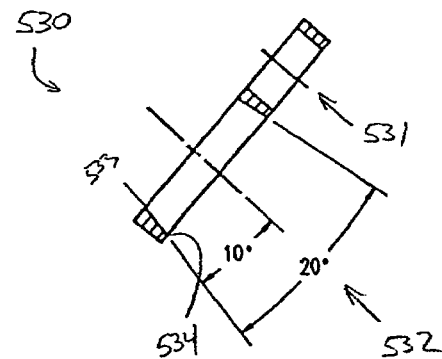
FIG. 48(d) is a cross-sectional view of the engaging device base member top portion of FIG. 48(a) taken at Section A-A.
Figure 49A:
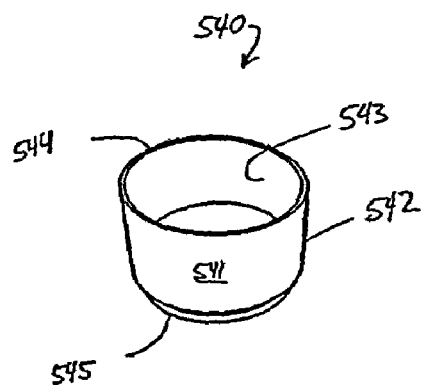
FIG. 49(a) is a perspective view of a drill cannula bushing for the variable locking instrument guide of FIG. 43.
Figure 49B:
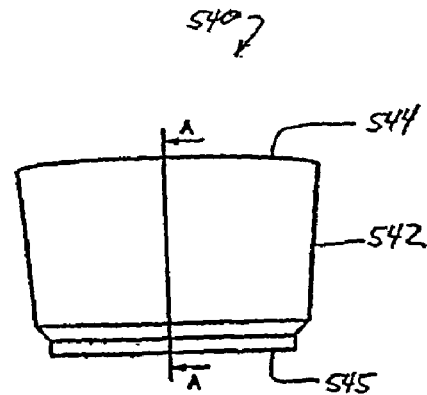
FIG. 49(b) is a side elevation view of the drill cannula bushing of FIG. 49(a)
Figure 49C:
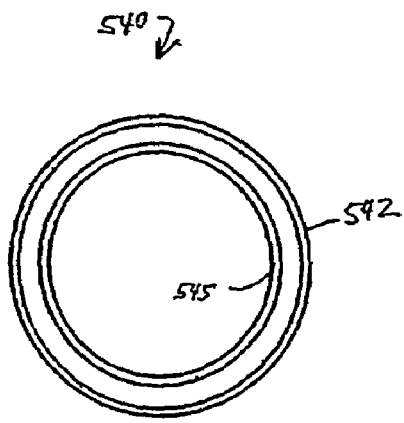
FIG. 49(c) is a bottom view of the drill cannula bushing of FIG. 49(a)
Figure 49D:
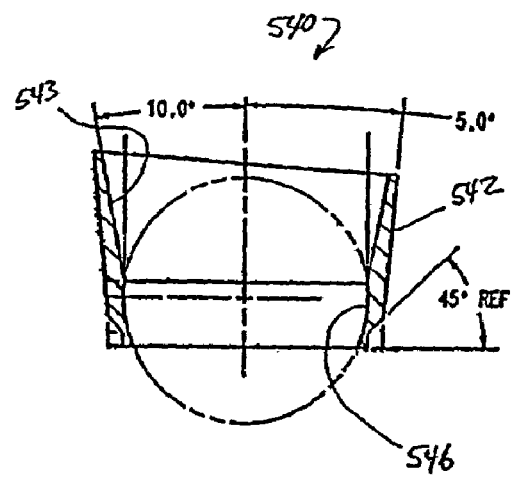
FIG. 49(d) is a cross-sectional view of the drill cannula bushing of FIG. 49(a) taken at Section A-A of FIG. 49(b)

Replace drawing sheet 30 containing Figure 48(d) with the attached replacement drawing sheet containing Figure 48(d).

Column 15, Line 60: replace "35(e)" with --47(e)--

Column 17, Line 36: replace "second" with --first--

Column 17, Line 37: replace "522" with --521--

Column 17, Line 47: replace "501" with --502--

Column 18, Lines 42-43: replace "detent 751 protrudes" with --detent protrudes--

Column 18, Line 45: replace "detent 751 is" with --detent is--

Column 18, Line 46: replace "spring 752 that bears against a stop 753. The" with --spring that bears against a stop. The--

Column 18, Line 49: replace "detent 751. Such" with --detent. Such--

Column 19, Line 29: replace "farther" with --further--

Column 19, Line 66: replace "farther" with --further--

Signed and Sealed this
Nineteenth Day of April, 2011

David J. Kappos
*Director of the United States Patent and Trademark Office*